United States Patent [19]

Sarrine et al.

[11] Patent Number: 4,890,247

[45] Date of Patent: Dec. 26, 1989

[54] AUTOMATIC ELECTROPHORESIS APPARATUS AND METHOD

[75] Inventors: Robert J. Sarrine, Beaumont; Henry A. Garsee, Kountz; Charles D. Kelley, Beaumont; Philip A. Guadagno, Vidor, all of Tex.

[73] Assignee: Helena Laboratories Corporation, Beaumont, Tex.

[21] Appl. No.: 211,761

[22] Filed: Jun. 27, 1988

Related U.S. Application Data

[62] Division of Ser. No. 26,465, Mar. 16, 1987, Pat. No. 4,810,348.

[51] Int. Cl.$^4$ .............................................. C25B 9/00
[52] U.S. Cl. .............................. 364/571.04; 204/182.8
[58] Field of Search ....................... 204/182.8, 299 R; 356/39, 344; 364/413.07, 571.02, 571.04

[56] References Cited

U.S. PATENT DOCUMENTS

| | | | |
|---|---|---|---|
| 4,097,149 | 6/1978 | Aladjem et al. | 204/299 R X |
| 4,162,208 | 7/1979 | Aladjem et al. | 436/516 X |
| 4,242,730 | 12/1980 | Golias et al. | 356/39 X |
| 4,244,797 | 1/1981 | Aladjem et al. | 436/515 X |
| 4,244,803 | 1/1981 | Aladjem et al. | 436/516 X |
| 4,360,418 | 11/1982 | Golias | 204/299 R |
| 4,391,689 | 7/1983 | Golias | 204/299 R X |
| 4,810,348 | 3/1989 | Sarrine et al. | 204/182.8 X |
| 4,827,780 | 5/1989 | Sarrine et al. | 73/864.21 |

Primary Examiner—Parshotam S. Lall
Assistant Examiner—Edward R. Cosimomo
Attorney, Agent, or Firm—Dodge, Bush & Moseley

[57] ABSTRACT

An electrophoresis machine is disclosed in which after a microporous support strip and a sample plate are placed in the machine, all electrophoresis processing, scanning and densitometer functions are automatically performed under computer control. The machine includes apparatus for automatic pipetting of liquid samples from the sample plate to the surface of the support strip, apparatus for applying electrophoresis current to the strip while simultaneously cooling it, apparatus for applying and spreading flourescent staining reagent to the strip, and apparatus for incubating the strip and subsequently drying it. A T.V. camera, mounted to a flourescent scanning box enlosing the application plate, in cooperation with digital processing equipment, electronically scans electrophoresically longitudinally displaced components of the samples for determining relative component densities. An alternative scanning apparatus including a collimator and photomultiplier is also disclosed.

2 Claims, 17 Drawing Sheets

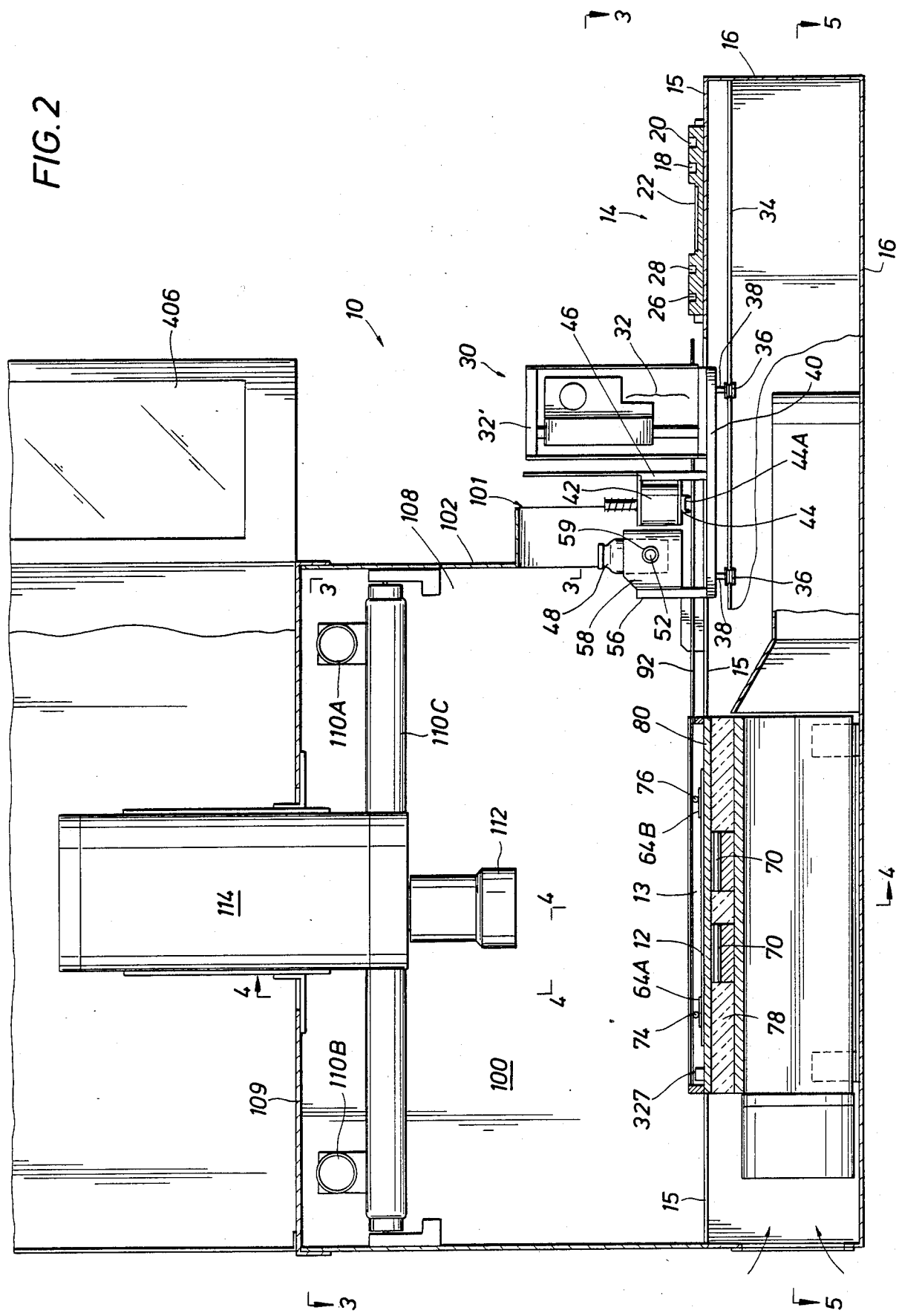

| | |
|---|---|
| DRIVE GANTRY BASE 40 TO COVER CLOSED POSITION | 517a |
| APPLY CURRENT TO SOLENOIDS 311 SO THAT ARMS 44 CONTACT COVER HOLES 93 | 517b |
| DRIVE GANTRY BASE 40 TO COVER 92 OPEN POSITION | 517c |
| DISCONNECT CURRENT TO SOLENOIDS DRIVER 311 TO RETURN ARMS 44 TO REST POSITION | 517d |
| DRIVE GANTRY BASE 40 TO REST POSITION | 517e |
| DRIVE GANTRY BASE 40 TO SUPPORT MEDIUM 12 | 519 |
| DRIVE REAGENT SUPPORT MOTOR 60 TO APPLY REAGENT TO SUPPORT MEDIUM 12 SURFACE AND RETURN | 520 |
| DRIVE GANTRY BASE 40 TO ELECTRODE/SPREADER BAR 74 | 522 |
| APPLY CURRENT TO SOLENOIDS DRIVER 311 SO THAT ARMS 44 GRIP SPREADER BAR 74 | 523 |
| DRIVE GANTRY BASE 40 TO SECOND WELLS 63 AND RETURN | 524 |
| DISCONNECT CURRENT TO SOLENOIDS DRIVER 311 TO RETURN ARMS 44 TO REST POSITION | 525 |
| DRIVE GANTRY BASE 40 TO ELECTRODE/SPREADER BAR 76 | 526 |
| APPLY CURRENT TO SOLENOIDS DRIVER 311 SO THAT ARMS 44 GRIP SPREADER BAR 74 | 527 |
| DRIVE GANTRY BASE 40 TO FIRST WELLS 62 AND RETURN | 528 |
| DISCONNECT CURRENT TO SOLENOIDS DRIVER 311 TO RETURN ARMS 44 TO REST POSITION | 529 |
| DRIVE GANTRY BASE 40 TO COVER 92 OPEN POSITION | 530a |
| APPLY CURRENT TO SOLENOIDS DRIVER 311 SO THAT ARMS 44 CONTACT COVER HOLES 93 | 530b |
| DRIVE GANTRY BASE 40 TO COVER 92 CLOSED POSITION | 530c |
| DISCONNECT CURRENT TO SOLENOIDS DRIVER 311 TO RETURN ARMS 44 TO REST POSITION | 530d |
| DRIVE GANTRY BASE 40 TO REST POSITION | 530e |

517 OPEN COVER (517a–517e)
518 APPLY REAGENT (519, 520)
521 SPREAD REAGENT (522–529)
530 CLOSE COVER (530a–530e)

Ⓔ

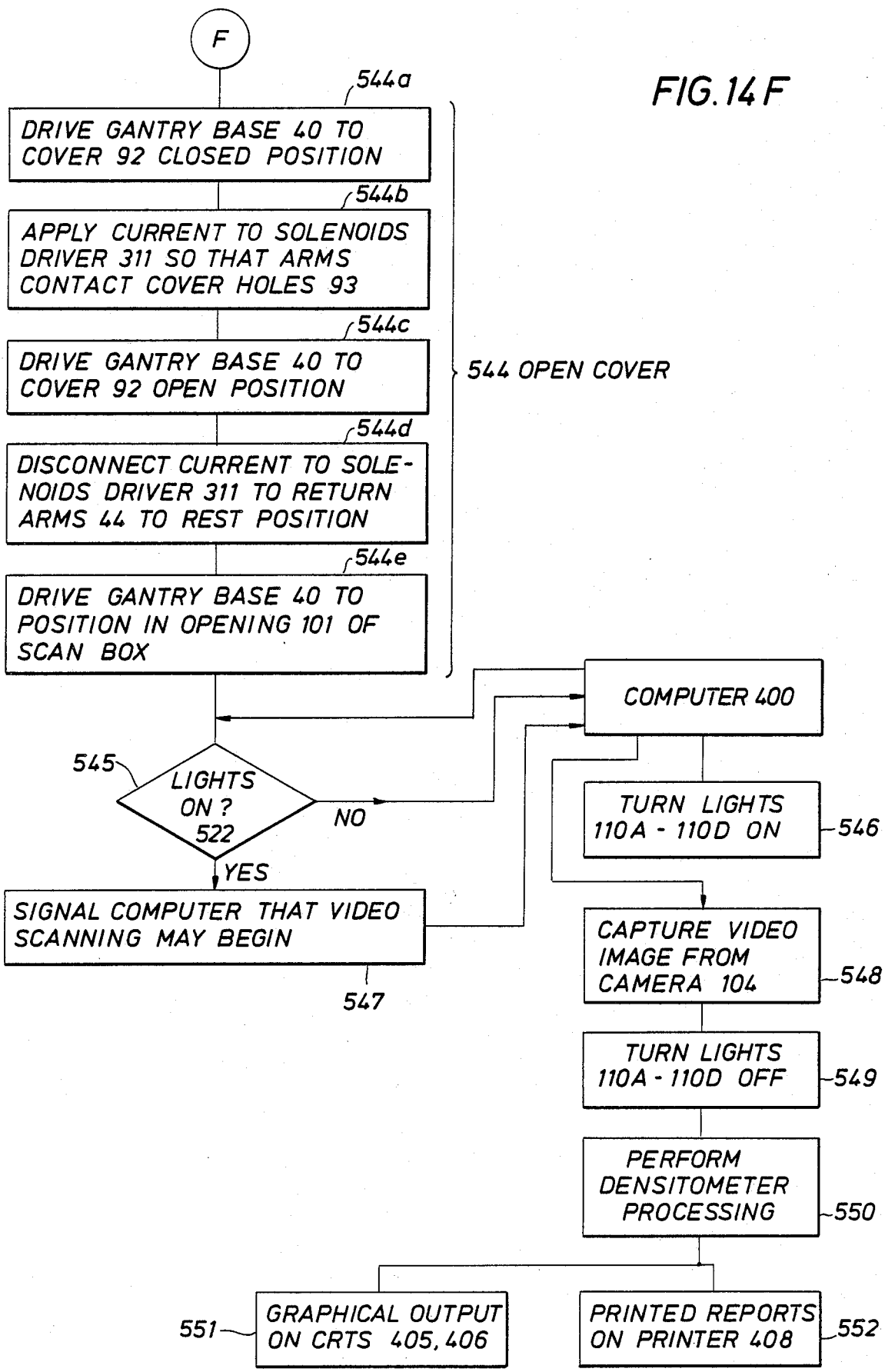

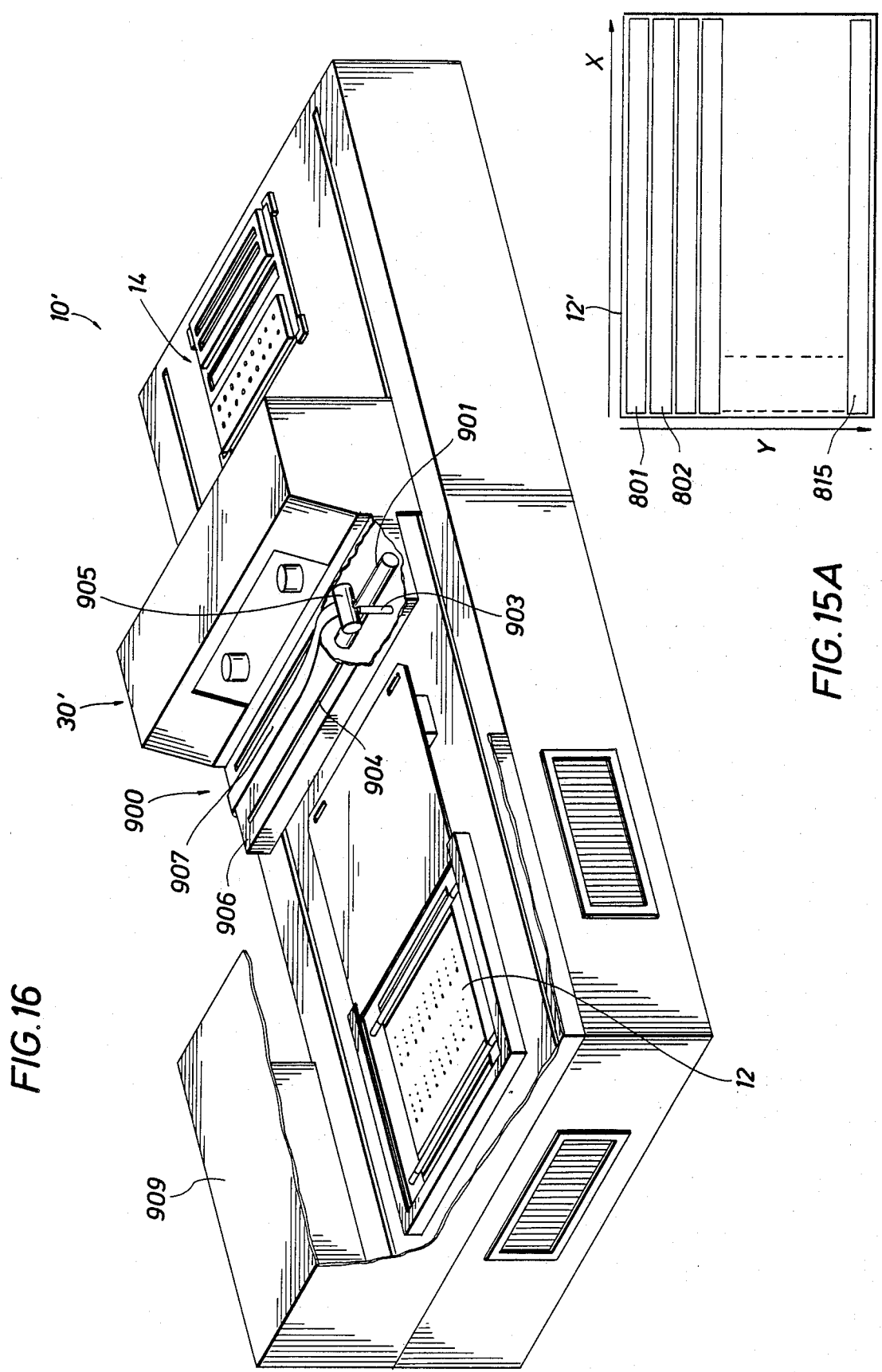

AUTOMATIC ELECTROPHORESIS APPARATUS AND METHOD

This application is a divisional of application Ser. No. 026,465, filed Mar. 16, 1987, now U.S. Pat. No. 4,810,348 issued Mar. 7, 1989.

BACKGROUND OF THE INVENTION

1. Field of the Invention

This invention is related in general to the field of electrophoretic analysis of liquid samples. In particular, the invention relates to an apparatus and method for completely automating the electrophoresis process beginning with the step of applying liquid samples to an electrophoresis support media and without moving the support media further including the steps of electrophoresing, staining, incubating, drying, scanning, and performing densitometry measurements on the scanned samples.

Electrophoresis is the science of moving charged particles in an electric field through a solid or semi-solid media. The technique is most commonly used in medical research in medical laboratories for analyzing various blood proteins.

2. Description of the Prior Art

In the diagnosing of ailments of human beings and animals, it is known that much information can be provided by an analysis of certain biological fluids such as blood serum proteins, lippo proteins, hemoglobin and isoenzymes. It is well known that electrophoresis is an effective method of separating the respective components of such fluids for a microscopic analysis or for employing optical densitometry techniques in analyzing the samples.

In the basic method of electrophoresis, charged molecules of the sample fluids are separated under the influence of an electrical field wherein the liquid sample to be examined is applied to a support medium having a buffer moistened porous surface. Because the various components of the fluid move at different rates through the support medium, the liquid sample may be separated into its respective components. Subsequent staining of the fractional components in the support medium may then be subjected to optical densitometry or other methods for examination.

The electrophoresis process has been performed through a series of manual steps for many years. The manual process typically has started with the operator preparing an electrophoresis chamber by filling appropriate cavities of the chamber with buffer solution. Buffer solution is a liquid used in the electrophoresis process to maintain the support medium surface in a moist condition and to provide an electrical interface to a power source applied to the chamber so that an electric field may be applied to the support medium. The support medium is typically a piece of MYLAR (trademark) backing which has been coated with a gel substance such as cellulose acetate or agarose. The liquid sample to be examined is typically a blood serum, but of course may be other liquids, the components of which may be moved through an electric field.

After the operator has prepared the electrophoresis chamber, he then applies as precisely as he can, consistent volumes of the samples to precise locations on the support medium. The operator then places the support medium into the electrophoresis chamber so that the edges of the support medium are immersed in two buffer cavities at each of its longitudinal ends. Electrophoresis is then performed using a precise and consistent high voltage applied for a precise and consistent interval of time across the buffer cavities.

After electrophoresis has been completed, the operator applies a uniform coating of staining reagent or stain to the surface of the support medium allowing a precise and consistent interval of time for the reagent and sample to chemically combine. The staining reagent is a liquid used after electrophoresis to chemically combine with the separated components of the fluid sample, causing its components to exhibit optical characteristics.

Next, the operator places the support medium into a temperature controlled oven and incubates it using a precise and consistent temperature and time interval. Incubation is the process of controlling the chemical reaction between the components of the liquid sample and the staining reagent by means of applying heat for a fixed interval of time.

Next, the operator dries the sample plate by increasing the oven temperature for a second precise and consistent temperature and time interval. The drying process stops the reaction between the sample plate and the reagent by removing water from the support medium.

One of the problems associated with the manual support medium preparation is that the liquid samples to be analyzed are multiply applied to the support medium which is to be subjected to electrophoresis. The samples may be applied to the support medium one at a time in serial fashion with a hand pipettor, but the hand pipettor must be rinsed with a cleansing agent and blotted before a new sample is aspirated and then applied to the strip. Applicators have been designed to apply fluid samples simultaneously or in "parallel" to the strips. Such applicators are described at page 61 of the General Products Catalog for 1984–1985 of Helena Laboratories with offices in Beaumont, Tex. Such applicators may apply eight, twelve or more samples to a microporous support medium and have the advantage of making the electrophoresis technique easier and more reproducible.

Such applicators however have been essentially non-automatic and have required cleaning of the applicator tips after each application to the support medium. A disadvantage of the prior art applicators is that there has been no means for automatically washing and cleaning the barrels of the pipettes during each cycle time so as to prevent contamination of each of the barrels during application of a new plurality of fluid samples to a new support medium. Another disadvantage of the prior art applicators is that there has been no means for precisely automatically applying a very small amount—of the order of one microliter—of sample liquid to a support medium. Another disadvantage of the prior art is that there has been no means for precisely automatically diluting a very small amount of the order of one microliter of sample fluid with a diluting liquid and precisely applying a very small amount of the diluted sample to a support medium.

There have been prior art apparatus and methods available for automatically performing electrophoresis and staining of the plurality of samples applied to a support medium. For example, U.S. Pat. Nos. 4,360,418 to Golias and U.S. Pat. No. 4,391,689 to Golias describe an automated electrophoresis and staining apparatus and method.

Such apparatus includes an electrophoresis chamber and a series of vats mounted upon a platform and arranged in a row where the vats are adapted to contain respectively a liquid stain and a series of plate processing solutions. The plate holder rack, having a horizontal open frame, supports an upright electrophoresis plate or support medium onto which has been applied a sample for electrophoretic fractionization. Such electrophoresis plate had to have been previously prepared by applying liquid samples either manually or by using one of the parallel applicators described above. The plate is nested within the chamber within an electrophoretic circuit for a predetermined time period. A power operated lift and transfer assembly is provided on the base and is adapted to lift, transfer and lower the plate holder rack and plate from the chamber progressively into each of the underlying vats for a predetermined period in a linear stepping motion maintaining the plate in an upright position at all times. It is noted that the staining process relies on chemical procedures for the staining process rather than the manual system described above where incubation and drying are used. Although the apparatus described above has many desirable features, it has a practical disadvantageous feature in that it requires providing a plurality of chemicals and wash solutions in the unit which must be maintained periodically.

Prior art apparatus and methods for optically scanning support media which have been subjected to electrophoresis and staining have used devices such as photomultiplier tubes, photodiodes or similar devices which produce an electric current or voltage output proportional to the light falling on such device. These devices are generally referred to as detectors. Prior art instruments employing these detectors are used for determining various physical properties of the samples which have been prepared by electrophoresis. The properties of interest concerning the separated bands of the sample are size and optical density or intensity of emitted light which is of a wave length different from that of the excitation light source. Separated bands of each sample which have been subjected to electrophoresis are known components of the sample under test and it is desirous that they be quantified for the purpose of aiding in medical diagnosis or research.

The known instruments which use the detectors referred to above generally find it necessary to use a blocking optical slit. The purpose of the slit is to allow the detector to "instantaneously view" a portion of the sample plate which is the same relative size and shape as the slit. The detector then produces an electrical current or voltage which is proportional in amplitude to the magnitude of the light detected. The current or voltage produced is then converted by means of an analog to digital converter and the resultant digital representation of the light magnitude is stored in an organized format in a digital computer memory.

Although an alternative embodiment of the invention described below uses prior art detectors in combination with other automatic electrophoresis apparatus, a preferred embodiment of the invention includes the use of video electronic scanning of the samples on the support medium which have been prepared by electrophoresis. Video electronic scanning is preferred in recognition of well known problems of using such prior art scanning detectors. One of the problems of using such prior art instruments is that the blocking slit requires a very precise width and length. If the length is too great, some of the detected light may actually be the result from an adjacent sample. If the length is too small, all of the light from the sample currently being scanned may not be detected. With a plurality of samples on a plate it may be necessary to change the physical slit size from sample to sample.

If the slit physical width is too great, it is possible that the light from adjacent bands of the plurality of samples being scanned could be detected causing the boundaries to be difficult, if not impossible, to determine. If the width is too small, it is possible that the detector output will be erratic and not yield correct proportional results.

Another disadvantage of the prior art slit/detector system is that in order that the entire sample be observed, it is necessary that each sample be mechanically scanned by moving either the detector or the sample plate. The movement must be at a very constant speed and free of vibration in order that the digital data being collected by the A to D converter is an accurate representation of both the optical density and physical size of the components of the sample.

In order that a plurality of samples may be scanned, it is necessary that the detector or sample plate be moved in yet another axis such that the scanner may scan a sample and then step over to the next sample and continue the scanning process. The step-over movement must be accurate and repeatable to insure that the detector is truly seeing the entire sample and only the desired sample.

IDENTIFICATION OF OBJECTS OF THE INVENTION

It is therefore a general object of this invention to provide in a single apparatus means for automatically applying a plurality of liquid samples to a support medium, automatically subjecting such samples on the support medium to the electrophoresis process, automatically staining, incubating and drying the support medium on which the components of the liquid samples have been separated into longitudinal bands, automatically electronically scanning such bands, and automatically performing a densitometric analysis to the data which results from such scans, thereby providing an analysis of each liquid sample.

It is another object of the invention to provide an apparatus and method by which the electrophoresis process may be accomplished without the need for the support medium being immersed in a buffer liquid to provide an electrical interface to the electrophoresis power source.

It is another object of the invention to provide a means for automatically staining a support medium after the electrophoresis step and without human intervention including the steps of applying reagent to the support medium, incubating the medium and drying it.

It is another object of the invention to provide a means for electronic scanning of the stained support medium without the need for human handling of the support medium after the staining step.

It is another object of the invention to provide a method for calibrating an electronic scanning system for use in electronic scanning of an electrophoresed support medium.

It is another object of the invention to provide alternatively a prior art slit/detector mechanical scanning apparatus in combination with a single apparatus for automatically applying a plurality of liquid samples to a support medium, automatically subjecting such samples to electrophoresis, automatically staining, incubating and drying the support medium on which the components of the liquid samples have been separated into longitudinal bands, and automatically scanning such bands with the slit/detector mechanical scanning apparatus.

SUMMARY

The objectives identified above as well as other advantages and features of the invention are provided in an automatic electrophoresis machine which automates electrophoresis testing of liquid samples. The machine includes a base on which an application plate is supported. A microporous support strip is placed on the application plate. A scanning box encloses the application plate.

A liquid sample plate is supported by the base at a position longitudinally separated from the application plate. The sample plate includes a plurality of liquid sample wells in one or more lateral rows. Prior to operation of the machine, liquid samples to be tested are placed in the wells. A robotic frame is provided for translating between the sample plate and the application plate through an opening in a side wall of the scanning box. The robotic frame carries a row of pipettes, one or more staining reagent bottles and one or more solenoids with associated plungers.

Under computer control, liquid samples from the sample plate are applied in a lateral row to the surface of the support medium strip. Electrode bars cooperating with vertically magnetized posts provide a lateral sheet of electrical current through the support medium strip for electrophoretically longitudinally displacing components of the liquid samples while the application plate is simultaneously cooled.

Under computer control, reagent is dumped from the reagent bottles onto the surface of the support strip, and the plunger is actuated to move the electrode bars across the surface of the strip to spread the reagent. Under computer control, the strip is then incubated and dried. A T.V. camera placed in the top of the flourescently lit scanning box generates an analog voltage signal representative of the longitudinally displaced components of the liquid samples. Alternatively a mechanical scanning apparatus disposed on the robotic frame may be used to produce such analog voltage signal.

Under computer control, the analog representation of the longitudinally displaced components of the liquid samples is converted to a digital representation of their density or light intensity as a function of their longitudinal/lateral coordinates of the support medium. Computer processing means determines the lateral separation and corresponding density of each component of each individual sample.

BRIEF DESCRIPTION OF THE DRAWINGS

The objects, advantages and features of the invention will become more apparent by reference to the drawings which are appended hereto and wherein like numerals indicate like parts and wherein an illustrative embodiment of the invention is shown, of which:

FIG. 2 is a side view of the automatic electrophoresis machine, partially in section, showing the robotic crane assembly, the sample/wash/blotting plate unit, the electrophoresis application plate, the microporous support medium, the scanning box and a video camera mounted atop the scanning box;

FIGS. 14A-14F illustrate a flow chart of logic blocks of the computer program stored in the digital computer and digital control circuitry for automatically controlling the electrophoresis process;

FIG. 15A illustrates a uniform support medium used to calibrate the camera lens system and shows computer templates established about scanning tracks corresponding to sample tracks or rows of an actual electrophoresis support medium;

FIG. 16 illustrates an alternative embodiment of the invention where mechanically driven scanning apparatus is disposed on the robotic crane assembly thereby as an alternative to the electronic video scanning apparatus of FIGS. 1-15.

DESCRIPTION OF THE INVENTION

Description of the robotic crane assembly

Figure 1:
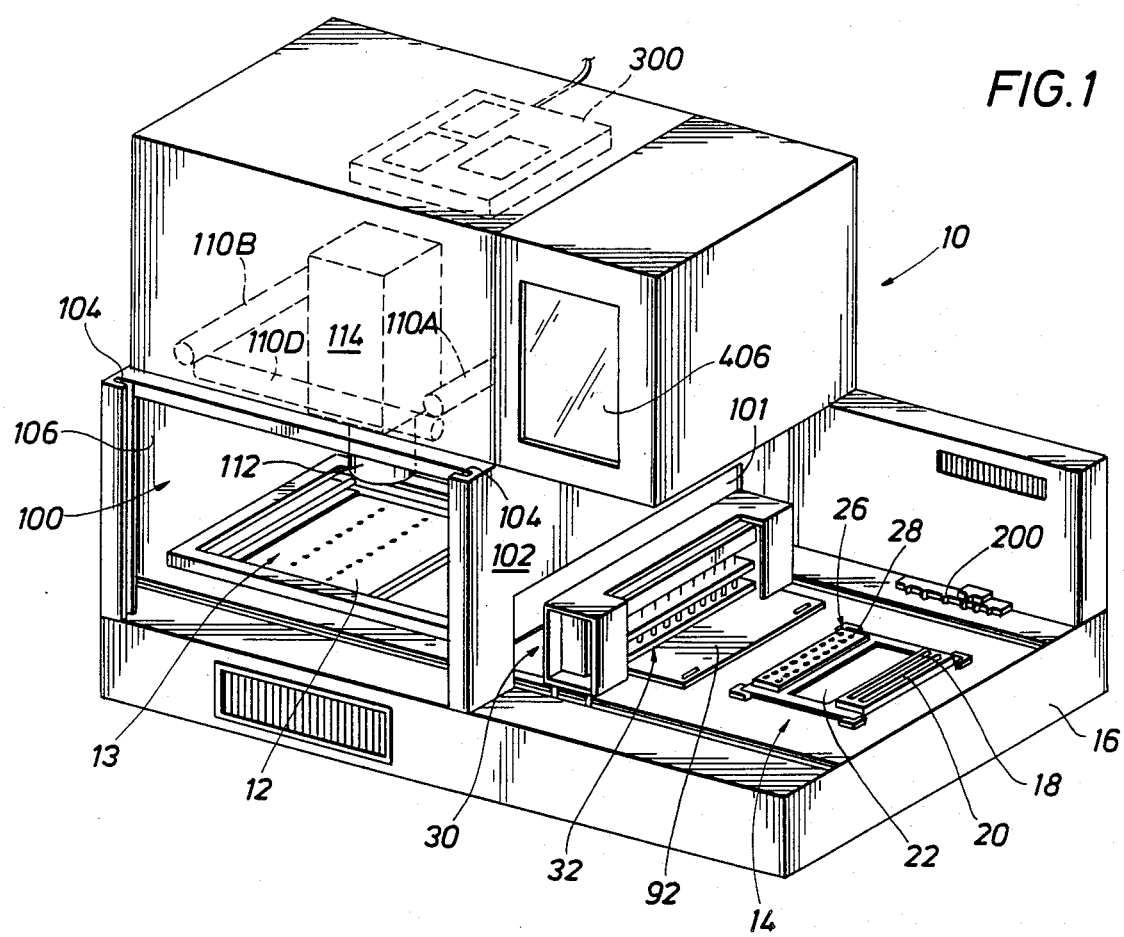
FIG. 1 is a perspective view of an automatic electrophoresis machine according to the invention having a robotic assembly between a sample plate unit and a microporous support medium in a scanning box wherein the front door of the scanning box has been removed to show its interior.
Figure 1A:
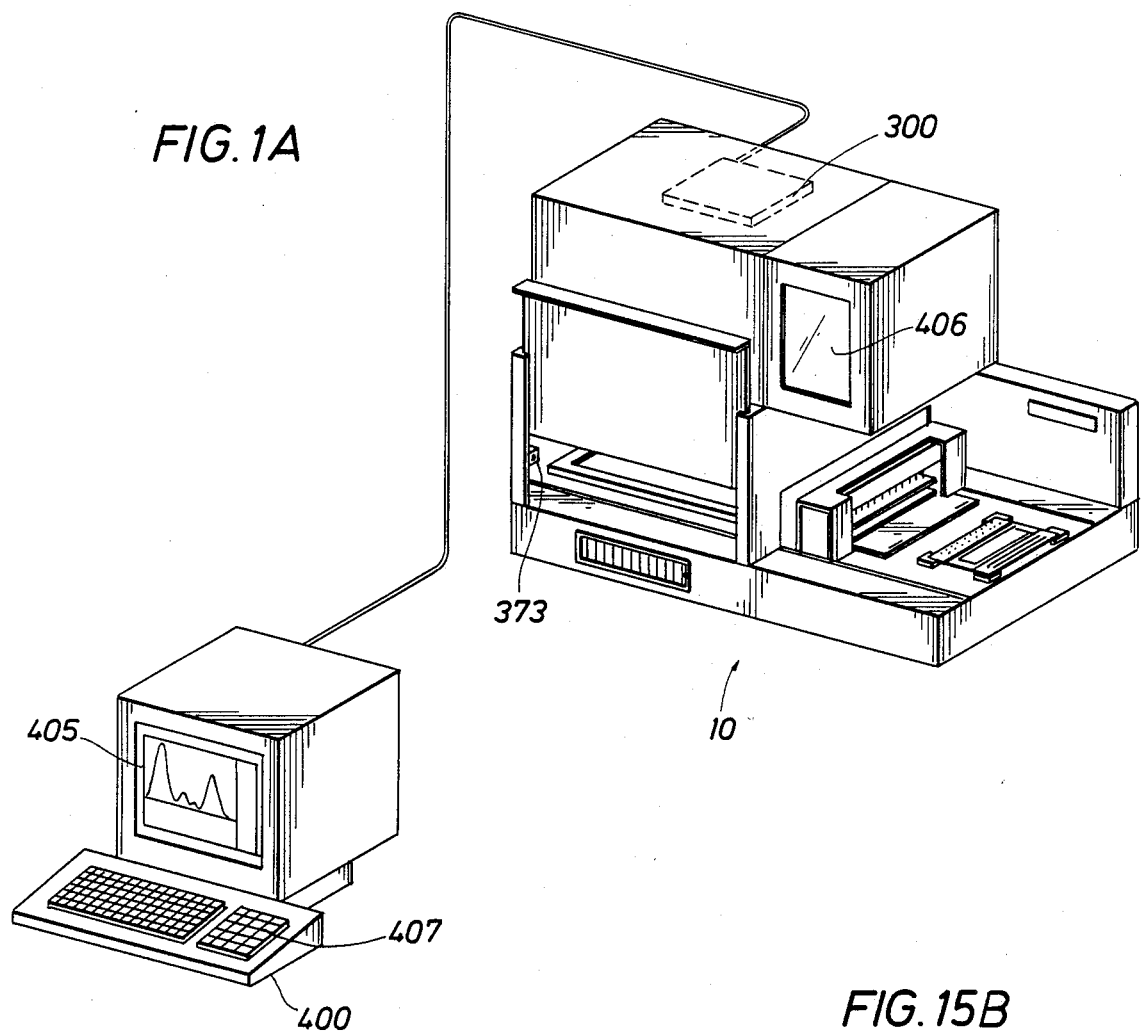
FIG. 1A shows the automatic electrophoresis machine with an associated computer which provides command and control signals to the digital control circuitry of the machine and which performs densitometric analysis of the sample plates after electronic scanning.

FIGS. 1 and 1A show the automatic electrophoresis machine 10 and its associated digital computer 400. As shown in FIG. 1, the automatic electrophoresis machine 10 includes a base 16 on which is mounted a sample plate unit 14 and an electrophoresis chamber 13 for mounting a microporous support medium 12. The support media which may be used in the electrophoresis process preferably includes a MYLAR backing on which a coating of cellulose acetate, agarose, or agar gel is deposited. The particular construction of the support medium according to the invention is described in detail below.

The automatic electrophoresis machine 10 includes a robotic crane assembly 30 adapted to move longitudinally between the sample plate unit 14 and the electrophoresis chamber 13. The automatic electrophoresis machine 10 includes a scanning box 100 having a side wall 106 and an entry wall 102 and a back wall. The front of the scanning box includes slots 104 in which a door (not shown) may be mounted for providing access to the scanning box 100 and for closing the scanning box 100 during electrophoresis processing and staining and electronic scanning of samples applied to the support medium 12. The door may include an interlock safety device in circuit with the electrophoresis high voltage supply such that when the door is in the open position, electrophoresis voltage within the chamber 13 is prevented. Such safety device prevents inadvertent operator shock from voltages as high as 2000-3000 volts in electrophoresis chamber 13. A cover 92, shown in its open position, may be slid longitudinally to open and close the electrophoresis chamber 13.

Flourescent lights 110A-110D are provided in the top of the scanning box for flourescently lighting the support medium 12 during electronic scanning by the camera 114/lens 112 system under control of the computer 400. Digital control circuitry 300 used to control the robotic assembly 30 and the electrophoresis process will be discussed in detail below. A videographics cathode ray tube 406 is mounted on the automatic electrophoresis machine and under computer 400 control provides monitoring information to the operator.

Turning now to FIG. 2, a front sectional view of the machine 10 shows details of the sample plate unit 14, the robotic crane assembly 30, the electrophoresis chamber 13 and the camera 114/lens 112 system within the scanning box 100. The machine 10 includes a base 16 on which a horizontal mounting plate 15 is provided for carrying the sample plate unit 14. The sample plate unit 14 is similar to that described in U.S. Pat. No. 4,827,780, issued May 9, 1989 in the names of Robert Sarrine and Henry Garsee and is assigned to the assignee of this invention. Such patent application is incorporated herewith showing detailed operations of automatically applying samples from a sample plate to a remotely disposed support medium.

The application plate 14, which may be manually supplied with liquid samples prior to placement on the machine 10, includes two lateral rows 26 and 28 of sample chambers in which liquid samples are provided which are to be automatically applied to the support medium 12. A blotting space 22 is provided on which blotting paper may be placed. Of course multiple blotting spaces, each with its own blotting paper may be provided if desired. A waste well and wash well is provided on the sample plate 14 by which the pipettes (including barrels and plungers) carried by the robotic crane assembly are cleansed and excess fluid dumped during the automatic application of samples. The pipette assembly 32 carried by the robotic assembly 30 is similar in construction and function as described in the above-mentioned patent application which is again incorporated herewith for its showing of the construction and function of the automatic application of samples from the sample wells of rows 26 and 28 to application on the support medium 12 in the electrophoresis chamber 13.

Figure 4:
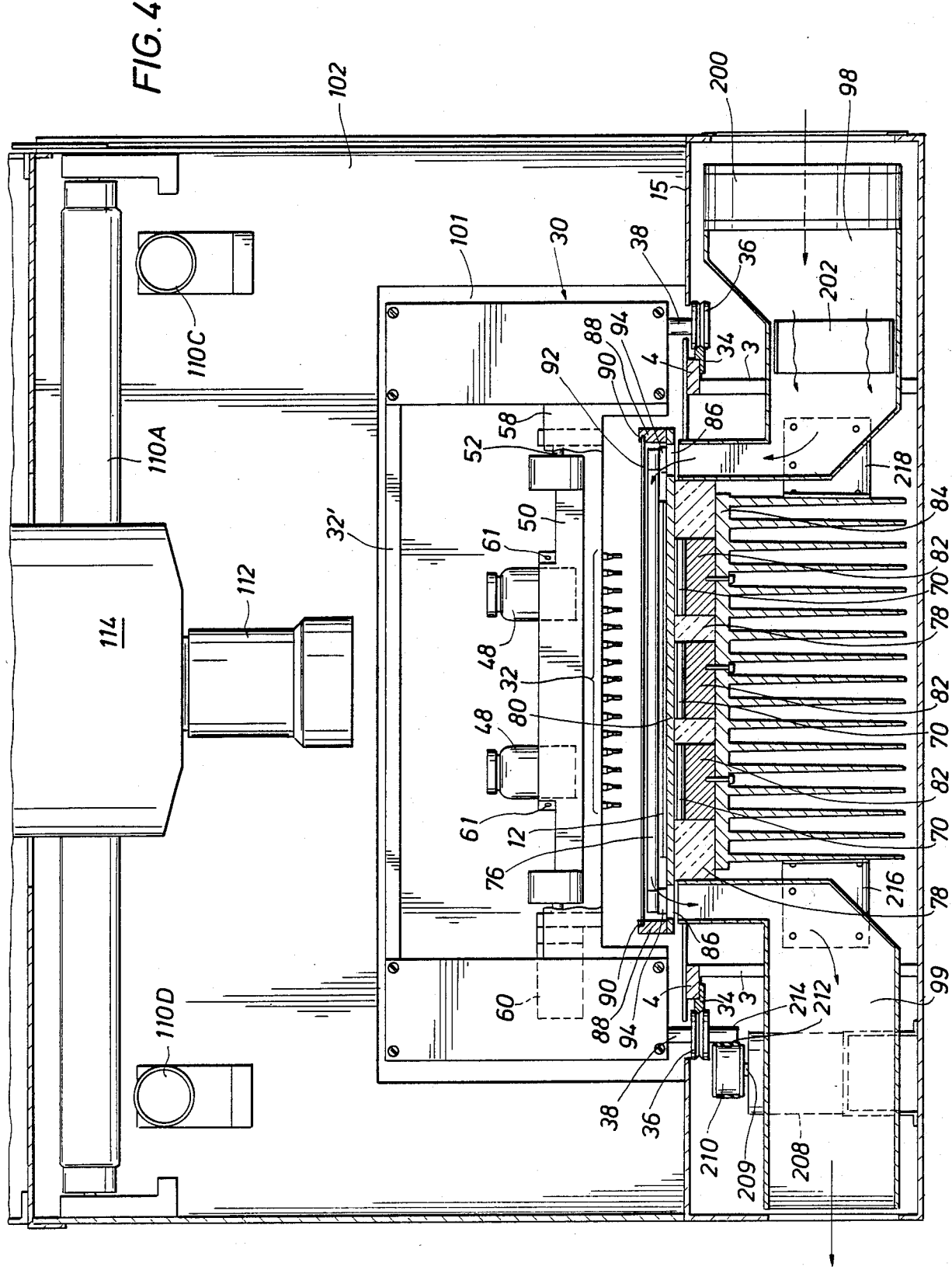
FIG. 4 is an end view taken along lines 4—4 of FIG. 2 and shows the robotic crane assembly in more detail and shows the construction of a heat sink associated with the cooling of the plate on which the microporous support medium is secured and shows a drying duct system by which the microporous support medium is dried after the reagent is provided to it and after it has been incubated.

As best shown in FIGS. 2 and 4, the robotic crane assembly 30 includes a frame 40 which is mounted for translation on robotic travel tracks 34 by means of rollers 36. The tracks 34 are supported by base 16. As shown in FIG. 4, the rollers 36 are attached to the frame 40 by means of shafts 38. The rollers 36 have grooves into which lateral projections of the tracks 34 extend, thereby allowing the robotic crane assembly 30 to be longitudinally moved between the sample plate unit 14 and the electrophoresis chamber 13. The tracks 34 are carried by horizontal members 4 secured to vertical members 3 which are supported by the base 16.

Figure 3:
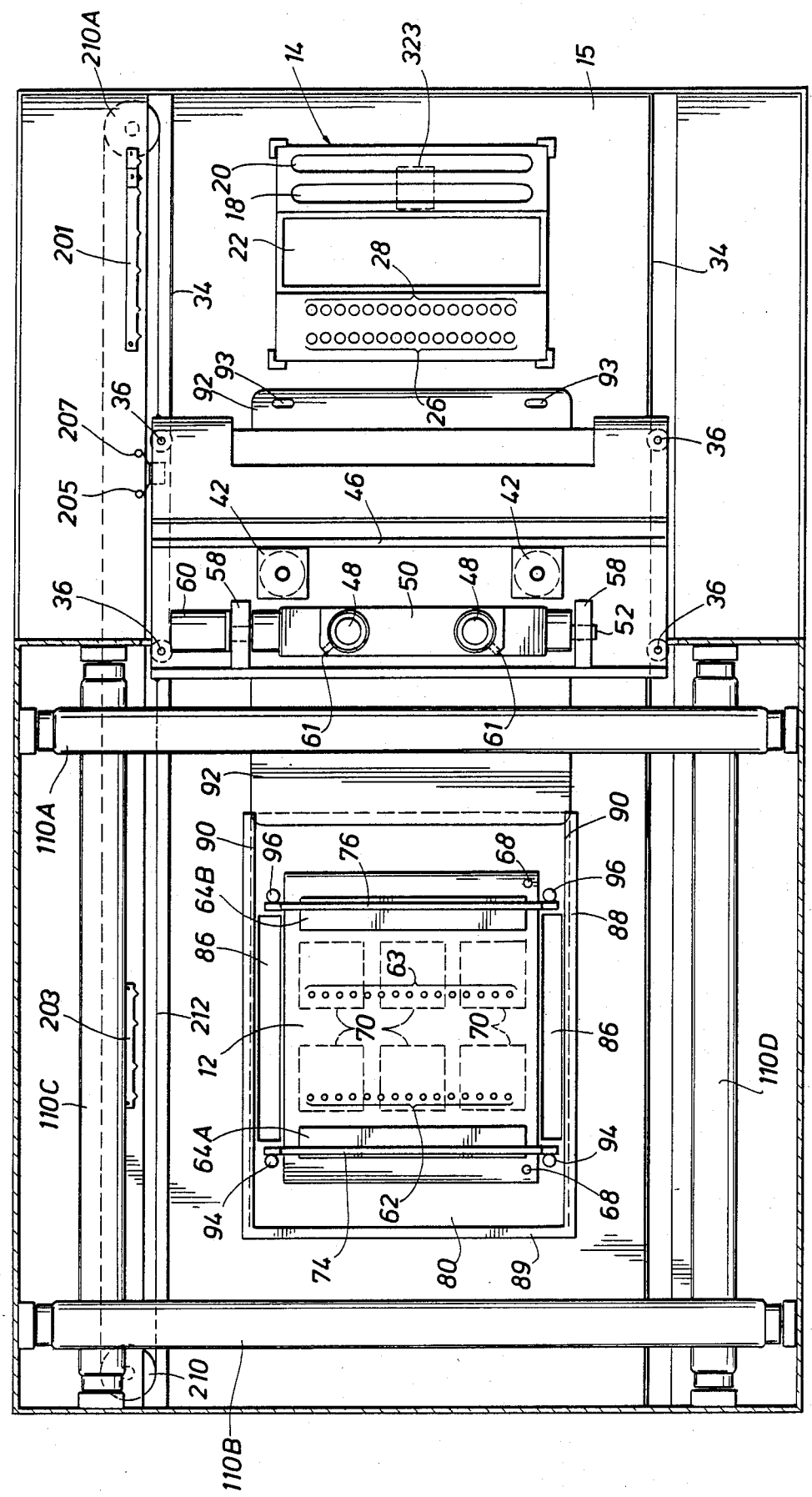
FIG. 3 is a plan view of the automatic electrophoresis machine according to the invention taken along lines 3—3 of FIG. 2 and showing a downward looking view of the sample/wash/blotting plate unit, the microporous support medium, electrode and spreader bar apparatus associated with it, and the robotic frame.

As shown in FIG. 4, a motor 208 mounted on base 16 has an output shaft 209 secured to a drive wheel 210. As shown in FIG. 3, a take-up wheel 210A is provided at the longitudinally opposite end of the machine. A continuous belt 212 driven by drive wheel 210 and looped about take-up wheel 210A is secured to an extension 214 of shaft 38 of the frame 40. Thus, by actuation of motor 208 the roller 210 drives belt 212 about take-up wheel 210A thereby translating the robotic crane assembly 30 with respect to the base 16.

Shown in FIGS. 2, 3 and 4, the robotic assembly 30 includes a vertical member 56 carried by frame member 40. Horizontal plates 58, secured to vertical members 56, support shafts 52 of bottle support member 50 as illustrated in FIG. 4. Two reagent bottles 48 are secured to bottle support member 50 by means of set screws 61. A reagent spread motor 60 mounted with respect to frame 40 is provided having its output shaft connected to shaft 52 of the bottle support member. Actuation of the motor 60 causes the bottle support member 50 to rotate until staining reagent provided in the bottles 48 is dumped onto the support member 12 when the robotic crane assembly 30 has been moved to a position over the electrophoresis chamber 13.

As illustrated in FIGS. 2 and 3, a vertical bar 46 extends upwardly from the frame 40 of the robotic crane assembly 30 and has attached thereto two solenoids 42. Each of the solenoids has a slotted arm 44 attached to its output shaft. Each of the slotted arms includes a slot 44A which is adapted to fit about the electrode/spreader bars 74 and 76 of the electrophoresis chamber to be described below. The slotted arms 44 are also adapted to fit within holes 93 of the electrophoresis cover 92 shown in FIG. 3.

From the foregoing it is seen that the robotic crane assembly of the invention is adapted to move longitudinally between the sample plate 14 and the electrophoresis chamber 13 and includes a pipette assembly 32, a pair of solenoids 42 and a pair of reagent bottles 48. The control of the pipette assembly for applying liquid samples from wells 26 and 28 to the electrophoresis chamber, the solenoids with their slotted arms 44 for spreading reagent and for closing the electrophoresis cover and the reagent bottles 48 for applying reagent to the support medium 12 is described below with respect to FIG. 6.

Another feature of the robotic crane assembly is described here in conjunction with FIGS. 1, 2 and 4. The robotic crane assembly 30 is adapted to move from outside the scanning box 100 through opening 101 in entry wall 102 of the scanning box 100. It can be seen that the top 32' of the pipette assembly has a lateral profile that fits relatively closely within the opening 101 as the robotic assembly 30 is passing into the scanning box. During the electronic scanning of the support medium 12 by the camera 114/lens 112 system, external light from outside the scanning box 100 is substantially prevented from entering into it by virtue of the dimensions of the exterior profile of the robotic assembly 30 fitting within the opening 101 of the entry wall 102.

Description of the Electrophoresis Chamber

As best shown in FIGS. 2, 3 and 4, the mounting plate 15 supports application plate 80 which is disposed laterally between the robotic travel tracks 34. The robotic crane assembly 30 is free to move on tracks 34 longitudinally above the application plate 80. As illustrated in FIG. 3, the application plate 80 includes one or more guide pins 68 for aligning and removably securing a support medium 12 such as an agarose strip. The agarose strip (support medium 12) includes two fluid reservoirs 64A, 64B at its longitudinal ends. The fluid reservoirs are each a raised gelatinous strip constructed of the same material as the top layer of the support strip, for example, agarose. The support medium 12 preferably includes two lateral rows of wells or indentions 62, 63 in the agarose material for accepting samples which are to be electrophoresed.

The electrophoresis chamber 13 has a first pair of electrode posts 94 extending vertically to a level substantially the same as the vertical level of the support medium 12. A second pair of electrode posts 96 are longitudinally separated from the first pair 94 and likewise extend above the support medium 12.

The first pair of posts 94 and the second pair of posts 96 are preferably constructed of a permanently magnetized material such as iron, yet are adapted also to conduct electrophoresing current. A first combination electrode/spreader bar 74 is disposed at one longitudinal end and a second combination electrode/spreader bar 76 is disposed at the other longitudinal end of the chamber 13.

Figure 3A:
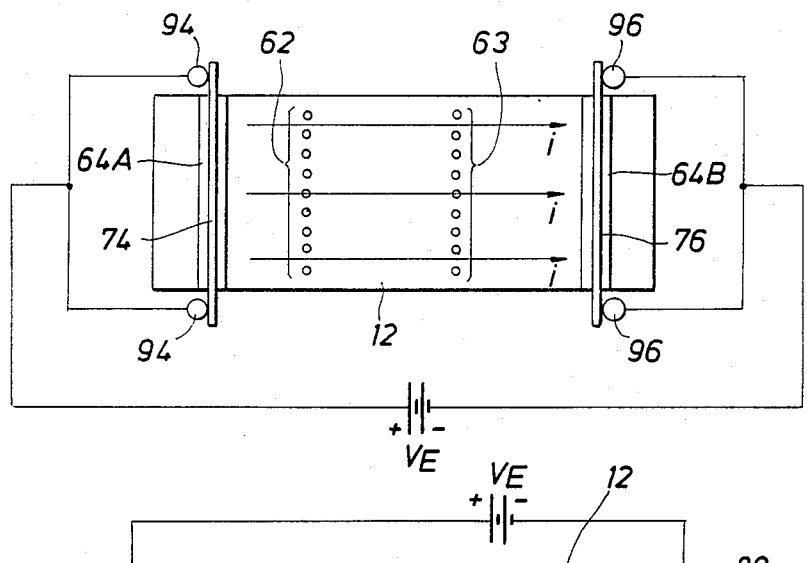
FIG. 3A is an electrical schematic diagram showing an electrophoresis voltage source placed across electrode post pairs at longitudinal ends of the support medium and illustrating the electrophoresis current flowing in a lateral sheet across the longitudinal dimension of the support medium.

The bar 74 and the bar 76 are preferably constructed of a ferro-magnetic material such as iron or steel. Thus when the electrode/spreader bar 74 and the bar 76 are disposed as illustrated in FIG. 3, they are held in place to electrode post pair 94 and electrode post pair 96 by the force of magnetism of the magnetic posts and the ferro-magnetic material of the bar. FIG. 3A illustrates that the posts 94 are connected to the positive terminal of a source of electrophoresis potential $V_E$ and the electrode post pair 96 is connected to its negative terminal.

The bar 74 in cooperation with the post 94 distributes the electrophoresing current laterally to the reservoir strip 64A and then across the support medium 12. The current moves longitudinally in a lateral sheet through the support medium 12 until it reaches the raised reservoir portion 64B of the support medium 12 where it then passes through the bar 76 to the posts 96 completing the electrophoresing circuit.

Figure 3B:
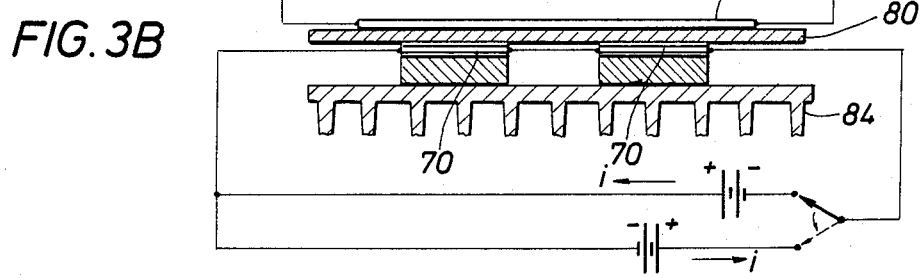
FIG. 3B illustrates the simultaneous application of current to a cooling/heating device disposed beneath the application plate on which the support medium is placed during the electrophoresis current application to the support medium and shows that current may be applied in the opposite direction to the device for heating.
Figure 3C:
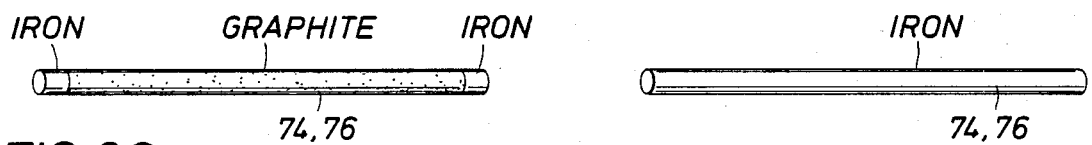
FIGS. 3C and 3D illustrate the combination electrode/spreader bars according to the invention.
Figure 3D:
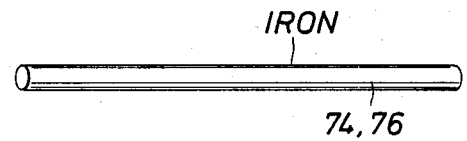
Figure 3E:
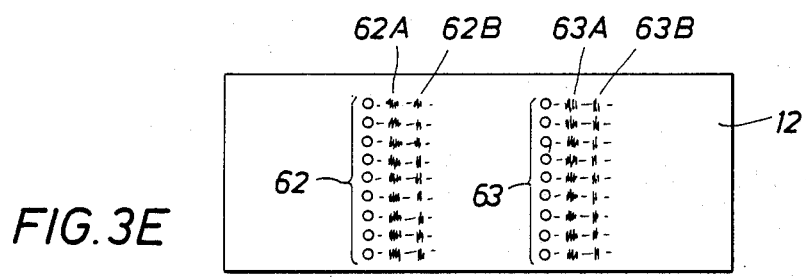
FIG. 3E illustrates the displacement of components of the samples applied to the support medium after the electrophoresis step has been performed.

FIGS. 3C and 3D illustrate that the bars 74, 76 may be constructed either entirely of ferro-magnetic material such as iron as in FIG. 3D or it may have its end portions constructed of a ferro-magnetic material having an intermediate portion constructed of graphite or stainless steel. Under the influence of the electrophoresing current flowing through the support medium 12, the components of the liquid samples in the sample indentions or wells of row 62 and row 63 are electrophoresed longitudinally. FIG. 3E illustrates the displacement of components of the material in the support medium 12 in lateral bands 62A, 62B for example with respect to sample row 62 and in bands 63A, 63B for example with respect to fluid samples in sample row 63.

Figure 3F:
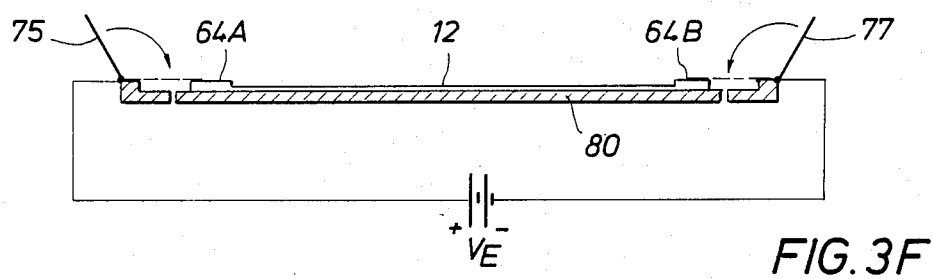
FIG. 3F illustrates an alternative arrangement for applying electrophoresis current to a support medium such that electrophoresis current is caused to flow in a lateral sheet across the longitudinal dimension of the support medium.

Other means for establishing current laterally across support medium 12 from raised portion 64A to raised portion 64B are of course possible. For example, FIG. 3F illustrates conductive hinges 75, 77 connected respectively to potential source $V_E$. The hinges fold outwardly to open plate 80 for placing support medium 12 on it. With the medium 12 in place, the hinges may be folded downwardly establishing electrical contact with raised portions 64A and 64B respectively.

Although the components of the liquid samples in rows 62 and 63 have been longitudinally displaced as shown in FIGS. 3A and 3E, the support medium 12 must be stained through a reagent application, incubation and drying process before they may be optically scanned with illuminated flourescent light as will be explained below.

So that the electrophoresing step may be accomplished more rapidly by the application of a higher electrophoresing current (which results in resistance heating of the support medium 12 and the application plate 80), two thermo-electric cooling/heating devices 70 (preferably six of them arranged as shown in FIG. 3) are provided beneath the application plate 80. The thermo-electric devices 70 are preferably Peltier devices which function to carry heat away from its top surface to its bottom surface on the application of electric current in one direction to the device. When current is applied in the opposite direction to the Peltier device, heat is applied to the application plate 80. An electrical schematic diagram of FIG. 3B illustrates that the application of current to devices 70 forces heat from the application plate 80 to a heat sink 84 thermally connected to its lower side. Current in the opposite direction forces heat from the heat sink 84 to the application plate 80.

FIG. 4 shows more clearly the placement of the Peltier devices 70 beneath the application plate 80 and illustrates that metallic conductors 82 are provided at the underside of the cooling devices and carry a finned heat sink 84 device beneath their lower side. Insulation 78 fills the spaces between and to the sides of the cooling devices 70.

Figure 5:
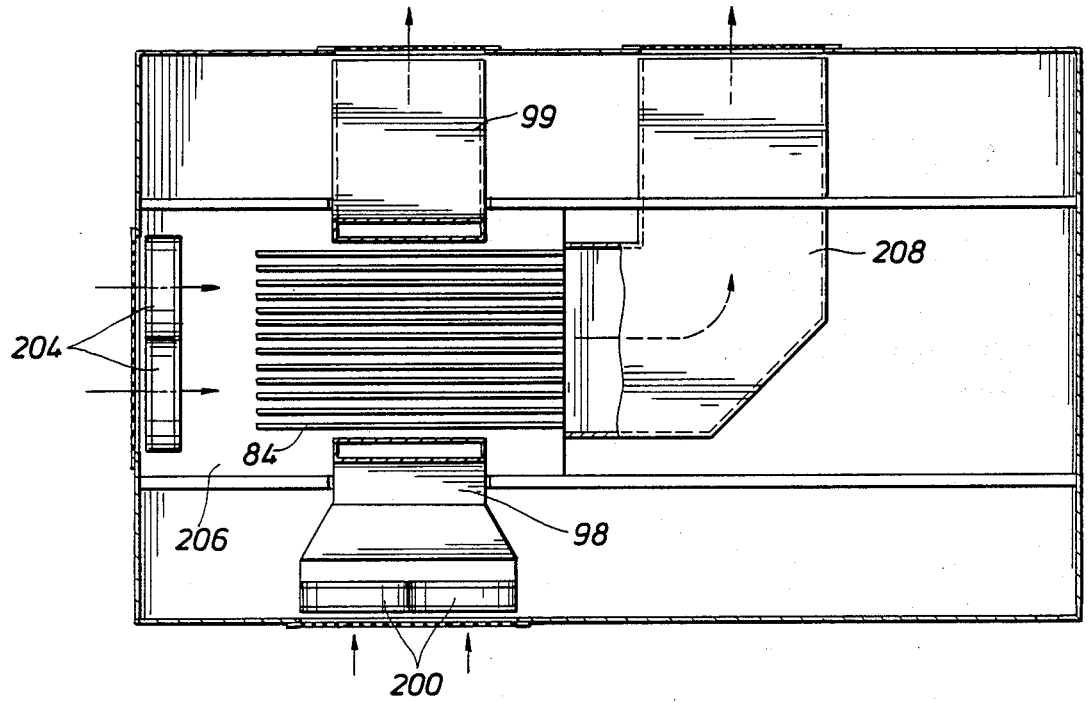
FIG. 5 is a downward looking view along lines 5—5 of FIG. 2 and shows the duct pattern by which the application plate and the microporous support medium removably secured thereto is dried and the duct means by which cooling air is brought from outside the machine across the heat sink to carry heat away from the plate during the electrophoresis process.

As shown in the cross-sectional view of FIG. 5, the finned heat sink 84 extends into an inlet cooling duct 206. Cooling air is brought into the duct 206 by means of fans 204 and passed over the fins of the heat sink 84 and pass outwardly to the rear of the automatic electrophoresis machine 10 via exit duct 208. When the circuits as illustrated in FIGS. 3A and 3B are actuated, that is during the electrophoresing process, current is applied to the Peltier cooling devices 70 in one direction by which the heat generated in the electrophoresing process is carried away and out of the machine by the cooling air from the duct 206 and out duct 208 as forced by cooling fans 204. The cooling apparatus illustrated is advantageous in the machine 10 in that a higher electrophoresing current may be applied, thereby reducing the time required for the electrophoresing step. The additional heat created by such higher current is effectively disposed of by the Peltier cooling devices.

After the electrophoresing step has been accomplished and reagent applied to the support medium 12 surface and spreading has been accomplished, all of which steps will be described in more detail below, it is necessary to incubate the support medium 12 with the staining reagent spread across its surface. Such incubation is accomplished by first closing the cover 92 to form a closed chamber about the electrophoresing chamber 13.

As illustrated in FIGS. 2, 3 and 4, a pair of vertically extending horizontal chamber bars 88 extend vertically from the plate 80. Longitudinal slots 90 are provided inwardly of the vertical bars in which the cover 92 may be slid longitudinally thereby covering and uncovering the electrophoresis plate 80. FIG. 3 illustrates the cover 92 in its open position and shows holes 93 in its end which are provided to cooperate with the slotted arms 44 of the solenoids 42 for opening and closing the cover.

As discussed above the Peltier devices 70 are provided beneath the application plate 80 with current provided to them in a direction opposite that for cooling when they are used during the incubation step (and the drying step). On actuation of an electric current (see FIGS. 3B and 6) in the opposite direction to Peltier devices 70, heat is applied directly to plate 80 which transfers that heat to the support medium 12 for incubating the reagent stain on the support medium.

FIGS. 2, 3 and 4 show the means by which drying air is applied across the surface of the support medium 12 after the incubation step has been completed. Longitudinally extending slots 86 are provided on lateral sides in the plate 80 outwardly of the space where support medium 12 is placed. Such slots are illustrated for example in FIG. 3 and may also be seen in cross-section on lateral sides of the end view of the application plate in FIG. 4. The righthand side of the slot 86 communicates with an inlet drying duct 98 while the lefthand rectangular slot in plate 80 communicates with the outlet drying duct 99

A heater element 202 is provided in the inlet drying duct 98 as well as a dryer fan 200. The inlet drying duct is mounted by means of a bracket 218 affixed to the metallic heat sink 84. The outlet duct is mounted by means of a bracket 216 likewise secured to the metallic heat sink 84. During the drying step, air is brought in from the front of the machine by means of the dryer fans 200 through inlet drying duct 98 and across the heating element 202, thereby applying drying heat to the surface of the support member 12.

Scanning Box

As best illustrated in FIGS. 2 and 4, the scanning box 100 includes four flourescent bulbs 110A–110D mounted in a rectangular pattern near the top of the box. A camera 114 having a lens 112 is mounted in the top wall 109 of the box and views downwardly toward the surface of the electrophoresis support member 12. Of course, in order for the scanning of the camera 104 to be effective, the cover 92 must be moved or displaced longitudinally outwardly so as to reveal the plate 12 to the camera 114/lens 112 system. As previously described of course, during the scanning of the electrophoresed and stained support member 12, exterior light is essentially blocked by means of the front cover (not shown) in slots 104 (FIG. 1) and by virtue of the robotic crane assembly 30 essentially filling the opening 101 in the entry wall 102.

Control Circuitry and Interfaces

Figure 6:
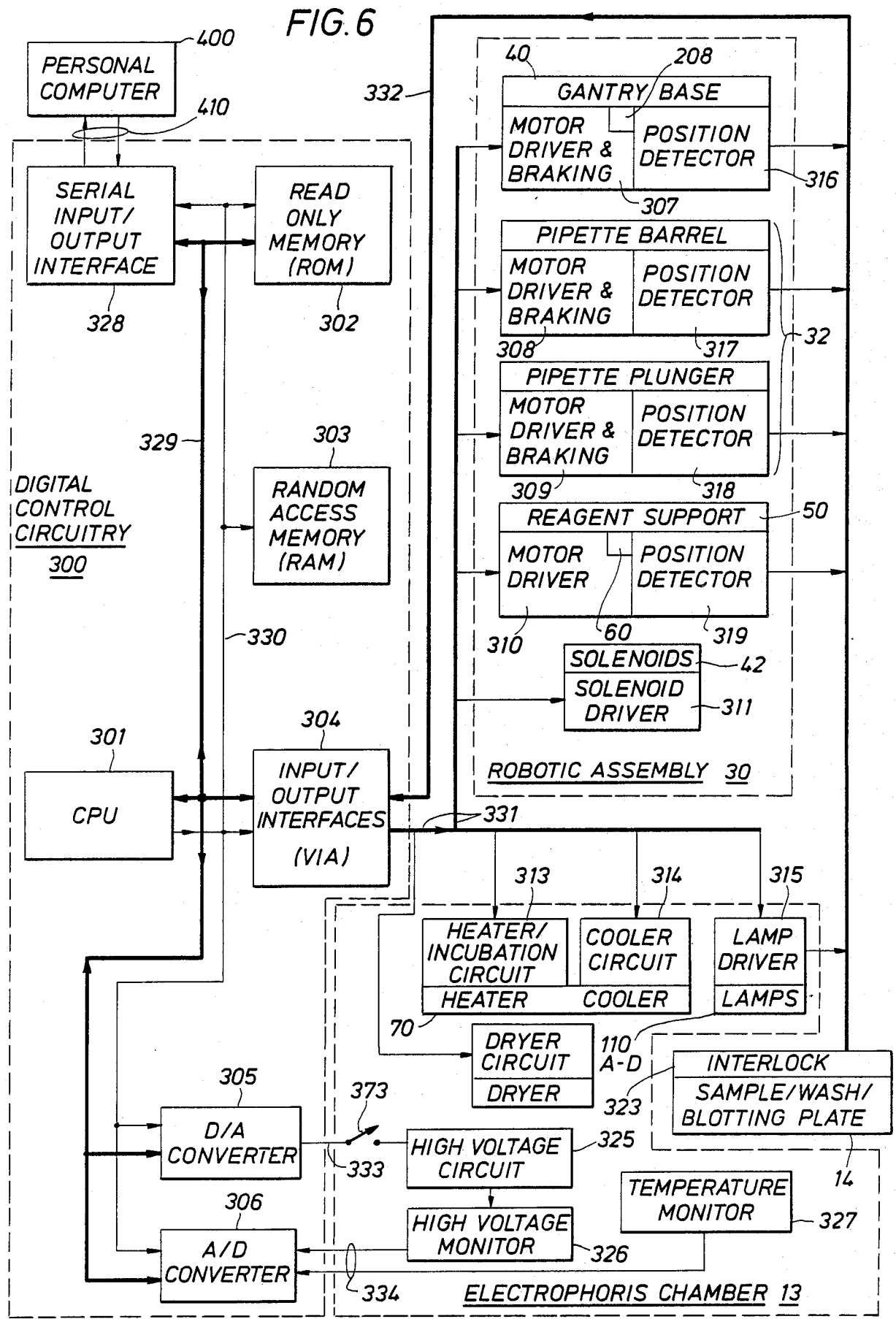
FIG. 6 is a schematic illustration of digital control circuitry and its interfaces with robotic assembly circuits and devices and with electrophoresis chamber circuits and devices.

FIG. 6 illustrates in block diagram form the interconnection between the digital control circuitry 300 as illustrated schematically in FIG. 1 and the robotic assembly elements 30 which control the movement of the robotic crane assembly. Various information and control circuits disposed in the electrophoresis chamber 13 are also illustrated. The digital control circuitry 300 is connected to the associated computer 400 by means of a bus 410. The connection of the computer 400 to the digital control circuitry 300 is shown physically in FIG. 1A and schematically in FIGS. 6 and 7 which will be discussed in detail below.

The digital control circuitry 300 includes a CPU 301 which is preferably a microprocessor chip commercially available as Motorola MC 6802. A read only memory 302 is provided for storing software control program instructions. A random access memory 303 is provided to store temporary data. Input/output interfaces (VIA) 304 includes programmable input/output interfaces and a system timer which is used to provide output control and input communication or monitoring functions and programmable time intervals. A digital to analog (D/A) converter 305 is used to provide analog output voltages to analog circuits in the electrophoresis chamber 13. Analog to digital converter (A/D) 306 is used to provide monitoring voltages from circuits in the electrophoresis chamber. A serial input/output interface 328 is used to interface input commands and output signals between the computer 400 and circuitry 300 via bus 410.

A databus 329 is provided as a bi-directional digital connection between the CPU ROM, RAM, VIA, D/A, A/D circuits and the serial input/output interface circuit. A bus 330 is an address bus used as a uni-directional digital connection from the CPU to the ROM, RAM, VIA, D/A, A/D circuits and the serial input/output interface. The address bus 330 is used by the CPU to uniquely select a device from or to which digital data is being transferred.

An output interface bus 331 is connected from circuit 304 and is used to connect the digital output of the CPU to the digital input of circuits being controlled by the CPU. Similarly, the input interface bus 332 is used to connect the monitor and detector circuits to the digital input of the CPU via input interface circuit 304.

Turning now to the robotic assembly 30, five separate elements are controlled: the gantry base 40, the pipette barrel and pipette plunger of the pipette assembly 32, the reagent support member 50 and the solenoids 42. A detailed description of the pipette barrel and the pipette plunger control is not described here, but their control is as described in detail in the previously filed U.S. patent application No. 853,201 to Messrs. Sarrine and Garsee. The previously mentioned application is incorporated herewith for a complete description of the operation and control of the pipette barrels and pipette plungers as they are used in applying liquid samples from wells 26 and 28 to the support member 12.

Gantry base or frame 40 control is by means of a motor driver and braking circuit 307 for controlling motor 208. The position detector 316 schematically illustrated in FIG. 6 is physically embodied by means of the sample cam plate 201, the application cam plate 203, and limit switches 205 and 207 illustrated in FIG. 3. The position detector functions by counting interruptions of the stitches 205 and 207 as they pass the cams on the sample cam plate 201 and the application cam plate 203.

The motor driver and braking circuit 308 of the pipette barrel and its position detector 317 as well as the motor driver and braking circuit 309 of the pipette plunger and its position detector 318 are as described in the above referenced patent application.

With respect to the reagent support member 50, a motor driver circuit 310 is provided under control of the CPU 301 and VIA circuit 304 to turn motor 60 in one of two directions when the gantry base 40 is in position over the support medium 12. A limit switch (not illustrated) serves as a position detector 319 associated with the shaft 52 of the bottle support member 50 as shown in FIG. 4.

A solenoid driver circuit 311 is provided in association with solenoids 42 so as to extend the slotted arm 44 to its downward position when a signal is applied to it.

An interlock circuit 323 is provided beneath the sample/wash/blotting plate 14 so as to signal the CPU via the input/output interface 304 that the sample plate 14 is in position and that the machine is ready to receive a start command from personal computer 400.

Turning now to the circuits of the electrophoresis chamber 13, a high voltage circuit 325 and a high voltage monitor circuit 326 are used to provide electrophoresis current to the support medium 12 as illustrated in FIG. 3A. The high voltage circuit 325 is responsive to a command from the CPU 301 via the D/A converter 305, D/A bus 333 and scanning box door interlock circuit 373. The monitoring signal from the high voltage monitor 326 is applied to the A/D converter 306 via bus 334.

Similarly, a temperature monitor circuit 327 applies its analog signal to the A/D converter 306 via bus 334 for recognition by the CPU 301. The temperature sensor or transducer 327 may be seen within the electrophoresis chamber 13 in FIG. 2. Digital control signals to Cooler/Heater (Peltier devices) 70 are applied from output bus 331 to a heater incubation circuit 313. Similarly, digital control signals to Peltier devices 70 are applied to a cooler circuit 314 from output databus 331.

Lamp driver circuit 315 responds to digital commands via bus 331 for controlling lamps 110A-110D in the scanning box 100.

Figure 7:
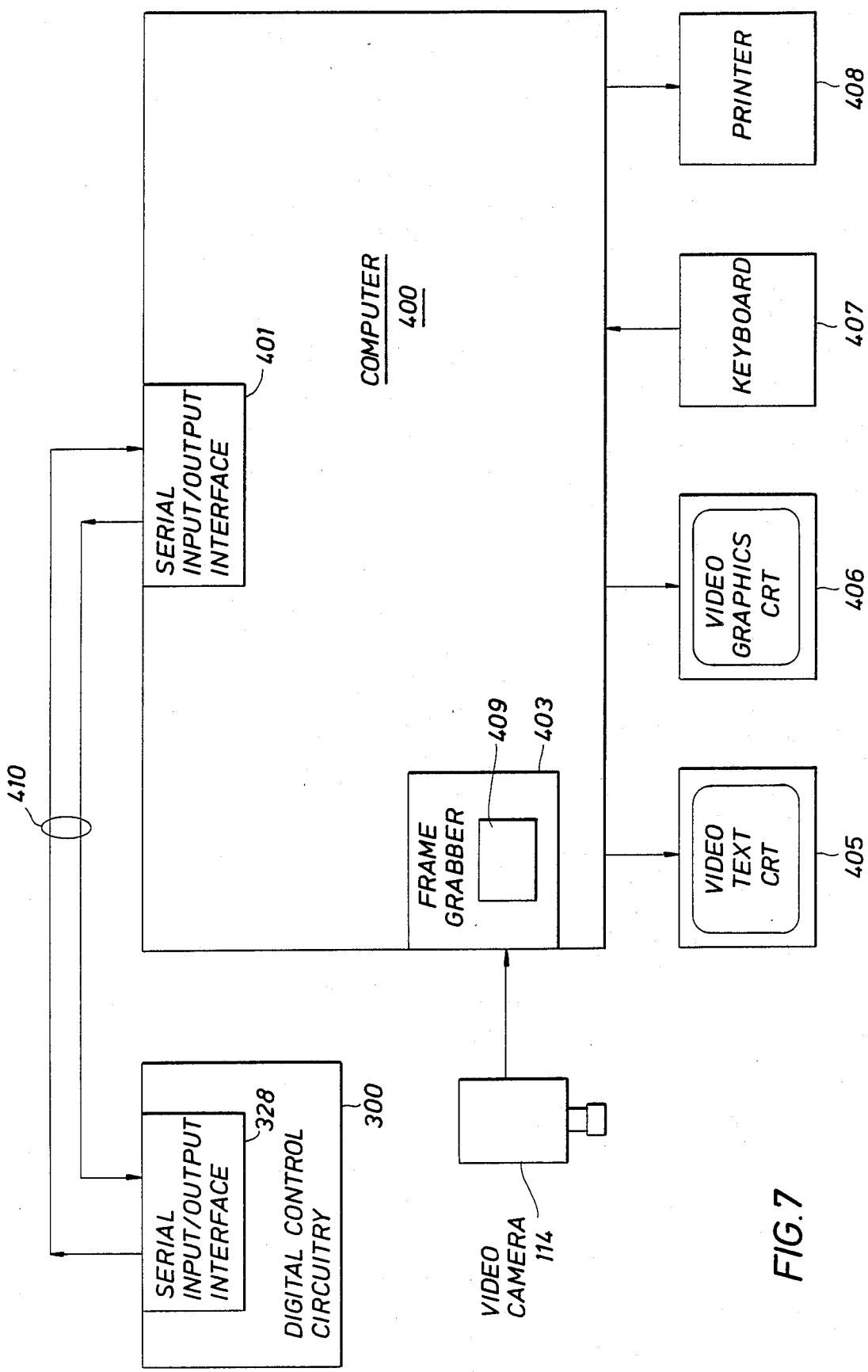
FIG. 7 is a schematic illustration of a computer associated with the automatic electrophoresis machine of the invention showing interfaces with the digital control circuitry of the machine, with the scanning camera and with peripheral devices for input/output communication with the computer.

Turning now to FIG. 7, a schematic description of the elements of the computer 400 indicates its connection to the digital control circuitry 300 via the serial input/output interface circuit 328 and bus 410. A serial input/output interface 401 provides the interface via the bus 410 for the computer 400. Preferably the computer 400 is a "Personal Computer" such as the Compact Desk Pro Model (Trademark). The computer 400 is used to communicate commands from the operator of the system of FIG. IA to the automatic electrophoresis machine 10 and to report data from it to the operator, analyze the digital data stored in the computer and to produce both graphic and text reports to the operator by means of output devices.

Input from the operator to the computer is by means of a keyboard 407 while printed output is by means of a printer 408. A videotext cathode ray tube 405 may be associated directly with the personal computer 400 while a videographics CRT 406 may be provided directly in conjunction with the automatic electrophoresis machine 10 as illustrated in FIG. IA.

Electronic Scanning and Calibration

The video camera 114 is preferably a vidicon T.V. tube which produces a serial analog voltage representation of its viewing area. A frame grabber 403 interfaces with camera 114 to convert the camera's serial analog output to a digital data representation. The frame grabber 403 stores such digital representation in the memory 409 of the frame grabber which subsequently produces both graphic and text reports of the analysis.

In operation, the camera 114 sees a viewing surface somewhat similar to FIG. 3E after the electrophoresis and staining processes have been automatically performed under control of the computer 400 and the digital control circuitry 300. When the flourescent lights 110A-110D are turned on, the camera scans the entire support medium 12. The camera produces analog video and synchronization signals. The instantaneous video voltage amplitude is a representation of the magnitude of the light emitted from the surface of the support medium. This analog output voltage is then converted as indicated above to a digital representation of a matrix of 512 columns by 512 rows of "pixels" by means of frame grabber 403. The synchronization signals are used to correlate the video analog data to precise locations on the sample plate 12.

Before the sample plate unit 14 and the automatic electrophoresis operation begins with the automatic electrophoresis machine 10, calibration of the camera 114 lens/112 system is performed. Calibration corrects for non-linear parabolic effects which may produce a non-uniform response of the intensity level of the individual pixels of the matrix of 512 columns by 512 rows as sensed by frame grabber 403.

In order to calibrate the camera 114/lens 112 system, a uniform test support medium 12', as illustrated in FIG. 15A is placed in scan box 100 on application plate 80. The test support medium 12 is one that has had no samples applied to it, and of course has not been electrophoresed, incubated or stained. The front door to the scan box is closed and the robotic crane assembly 30 is moved into the opening 101 so as to simulate actual scanning conditions where substantially all outside light is blocked from entry into the scan box 100. Next, the ultraviolet lamps 110A-110D are turned on, and the camera 1 14/lens 112 system is turned on. The frame grabber 403 (FIG. 7) receives a "snap shot" of the plate; that is, the intensities of each of the pixels of the 512 by 512 matrix are stored in memory 409.

Next, templates 801, 802, . . . 815 are electronically defined under program control about the fifteen scan tracks corresponding to the 15 sample tracks or rows of an actual support medium 12 when placed on application plate 80. The "height" or "y" direction of each track is about 1/15the of the memory's 409 height (approximately 34 pixels). The width or "x" direction of each track is equal to the total width, 512 pixels, of the total width of the image memory. These 15 tracks correspond to the location of the sample tracks of the electrophoresis plates to be scanned later.

Within each of the 15 tracks, the two dimensional array of pixel intensity data is converted into a single dimensional array of data by summing and averaging the pixel values in each of the 512 vertical columns within each of the approximately 34 pixel rows. That is for each track, at each vertical column, the intensities of the 34 pixels in that track are summed and divided by the number of pixel rows, e.g., 34. As a result, each of the 15 tracks is represented by a row vector of average intensities as a function of the x dimension of pixels running from x=1 to x=512. A search of each of the average intensities in this "averaged intensity" matrix of 15 by 512 intensity values is then made to determine the greatest value, $I_{max}$.

Next, each average pixel intensity in the averaged intensity matrix (15 by 512) is divided into the value of $I_{max}$ Each element in the matrix is replaced by the result of such division. Thus each element of the matrix becomes a correction factor of a "correction factor matrix" to be applied to an actual support medium during operational scanning after the support medium 12 has had samples applied to the two sets of fifteen sample wells, and after steps of electrophoresis, staining, incubation, drying, etc. have been automatically performed.

Figure 15B:
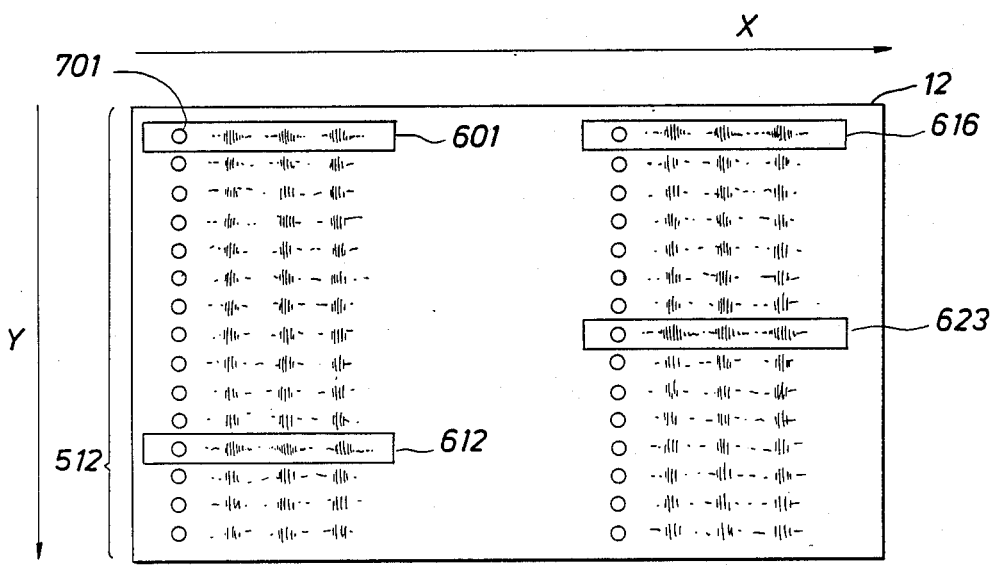
FIG. 15B illustrates electronic templates created under program control for automatically creating pixel boundaries about each of the electronic images of the electrophoretic patterns after automatically performing the electrophoresis process of a plurality of samples.

FIG. 15B illustrates electronic templates such as 601, 612, 616, 623 which are formed, under computer programming control, to define automatically the analysis area of each of the 512×512 pixels stored by frame grabber 403 for an actual support medium 12 which has been automatically electrophoresed. The "y" axial dimension of the templates are the same as each of the 15 calibration tracks described above during calibration. For example, the template 601 is predetermined to fit about the longitudinal electrophoresis pattern of the sample placed on support medium 12 at well 701. Because the medium 12 is physically located at a predetermined location on application plate 80, and because the camera 114/lens 112 is fixed with respect to application plate 80, the electronic template 601 is assured of precisely fitting about the electrophoresis pattern for the fluid sample at well 701. Programmed electronic templates are provided for each of the samples.

The data in each of the templates is then averaged over the pixels in the y rows inside the template to produce a single representation of density as a function of electrophoresis spreading distance x for each of the samples. Next, the average intensity valves for each x pixel position in each template is multiplied by a corresponding correction factor stored in the correction factor matrix described above. Such data is then stored in an organized format in the digital memory 409 of the computer 400 where a densitometric analysis may be performed. U.S. Pat. No. 4,242,730, assigned to the assignee of the invention described herein, describes a prior microprocessor— controlled densitometer. The 4,242,730 patent, incorporated herein, describes how digital representations of the scanned samples may be processed to produce an analog display on a CRT like display 405 illustrated in computer 400 of FIG. 1A. An operator may edit the visually displayed density curve.

It is advantageous to use a video camera or a similar device such as a CCD array because the entire sample plate may be scanned in one-thirtieth of a second. Such scanning includes information about all thirty samples for example, as shown in FIG. 3E. The data may be organized by the computer in a two-dimensional array of data and therefore allows the computer to not only exactly define individual longitudinal components of the sample but also to exactly determine sample boundaries in the event that sample separations do not occur in a parallel Additionally, the sample data may be enhanced by removing or reducing noise artifacts by repeating the scan and averaging the results.

Mechanical Scanning

There may be circumstances where advantages of electronic scanning of the in situ electrophoresed support medium may not be indicated. Cheaper manufacturing costs may dictate the use of a prior art mechanical blocking slit and detector assembly 900 as part of the robotic assembly 30' of FIG. 16. The automatic electrophoresis machine 10' of FIG. 16 is substantially the same as machine 10 of FIG. 1 except that assembly 900 provides mechanically driven electronic scanning as an alternative to the stationary video electronic scanning of the video camera 114/lens 112 system of FIG. 1.

The scanning assembly 900 preferably mounted on the forward side of robotic assembly 30', includes a fixed flourescent tube 901, collimator 903 and photomultiplier tube 905. The tube 901 is disposed inside the cover 906. The collimator 903 is disposed in a lateral slit 904 in the cover and faces downward toward the support medium 12 during scanning. The photomultiplier tube 905 is responsive to light transmitted via collimator 903.

A motor, not show, under microprocessor control is provided to step the collimator 903/photomultiplier tube 905 laterally across the electrophoresed support medium 12 after sample fluid application, staining, incubation and drying as previously described An electrical service loop or cable is provided between the photomultiplier tube 905 amplifier/analog to digital converter (not shown)for input of scanning signals to computer 400. Service loop 907 may also be connected to digital control circuitry 300 (FIG. 6) for controlling flourescent lamp 901 illumination during scanning. Longitudinal stepping across support medium 12 during scanning is accomplished by incrementally translating robotic assembly 30' longitudinally with motor 210 (FIG. 3). As show above, the mechanical blocking slit and detector assembly 900 generates electrical signals representative of the intensity of longitudinally separated components of the electrophoresed and stained samples on support medium 12.

FIG. 16 illustrates the robotic assembly 30' before it is moved longitudinally above support medium 12. It should be appreciated that scanning box 909 may be constructed with less height than scanning box 100 of FIG. 1 because there is no need to have a camera lens system with the scanning apparatus of FIG. 16.

Operation of the Electrophoresis Machine

After the operator has installed the sample plate unit 14 in position on the base of the machine as indicated in FIG. 1 and after a support medium strip 12 has been placed on the application plate 80 as indicated in FIG. 3, a door is closed in front of the scanning box 100 and the operator enters a start command via keyboard 407 of computer 400. It is to be understood that the liquid samples to be analyzed have been placed in the pair of well rows 26, 28 of the sample plate unit 14. Each well row preferably includes fifteen separate wells. A standard liquid sample may be placed in one of the wells for analysis comparison. It is also understood that blotting paper may be put into the blotting space 22 and that wash well 20 has previously been filled with wash water. The placement of the sample plate unit 14 on the base of the machine sends a signal over bus 332 to the digital control circuitry 300 as shown in FIG. 6. The computer 400 then receives an indication that the automatic processing may proceed under digital control.

Figure 8:
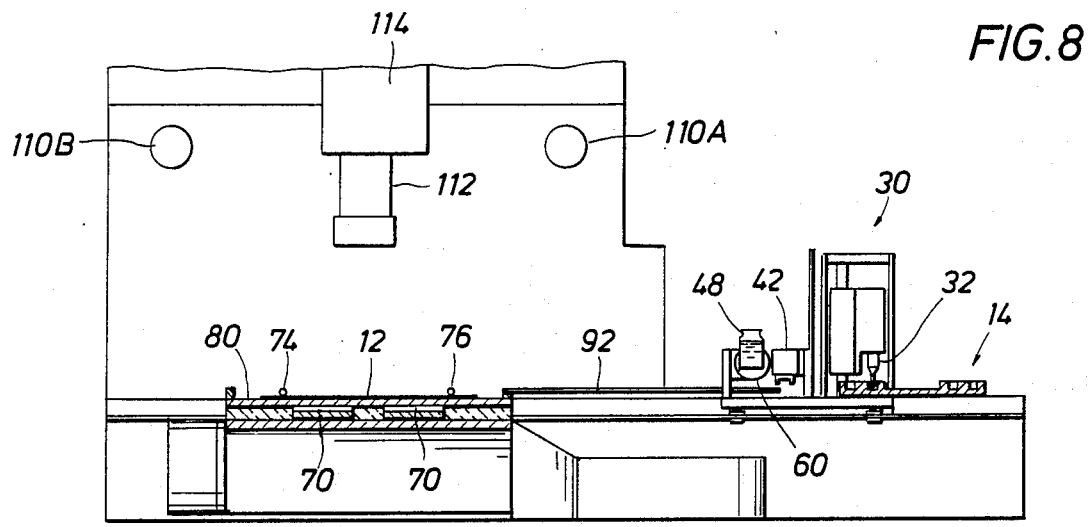
FIGS. 8–13 are schematic representations of the various steps by which the robotic crane assembly applies samples to the microporous support medium, applies reagent to it after electrophoresis has been conducted, and by which the reagent is spread across the surface of the microporous support medium and illustrate the electronic scanning of the support medium after incubation and drying of it.

FIGS. 8-13 illustrate significant steps in the automatic processing of the liquid samples stored in wells of rows 26 and 28 of the sample plate unit FIG. 8 illustrates that the pipette assembly draws samples and individual pipettes of a predetermined amount. As indicated above such operation is described fully and completely in the previously filed U.S. application 853,201.

Figure 9:
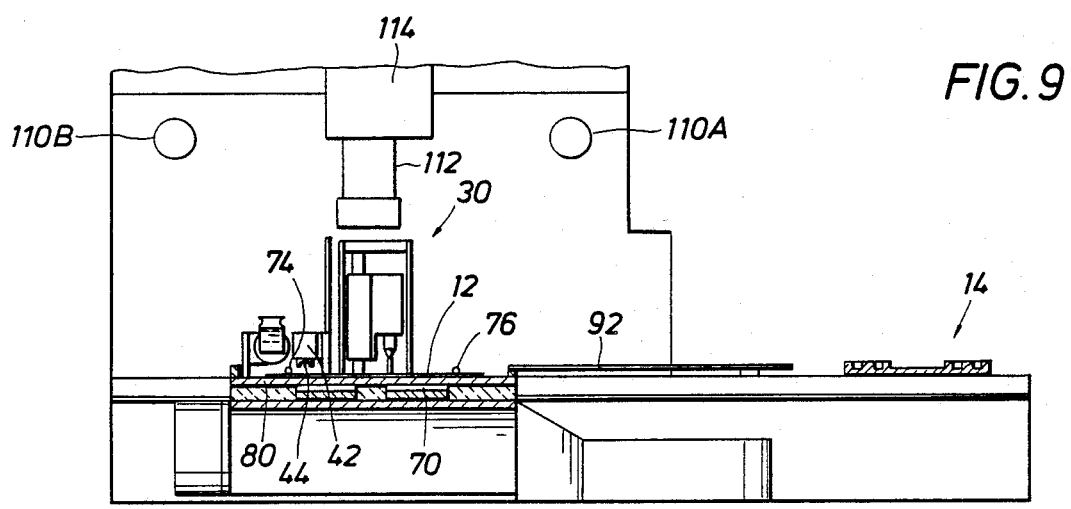

FIG. 9 shows that the robotic assembly 30 has been longitudinally moved to the area of the support medium 12 and that the fluid samples are applied in a row on the surface of the support medium. It is noted that the cover 92 of the electrophoresis chamber is in its open position.

Figure 10:
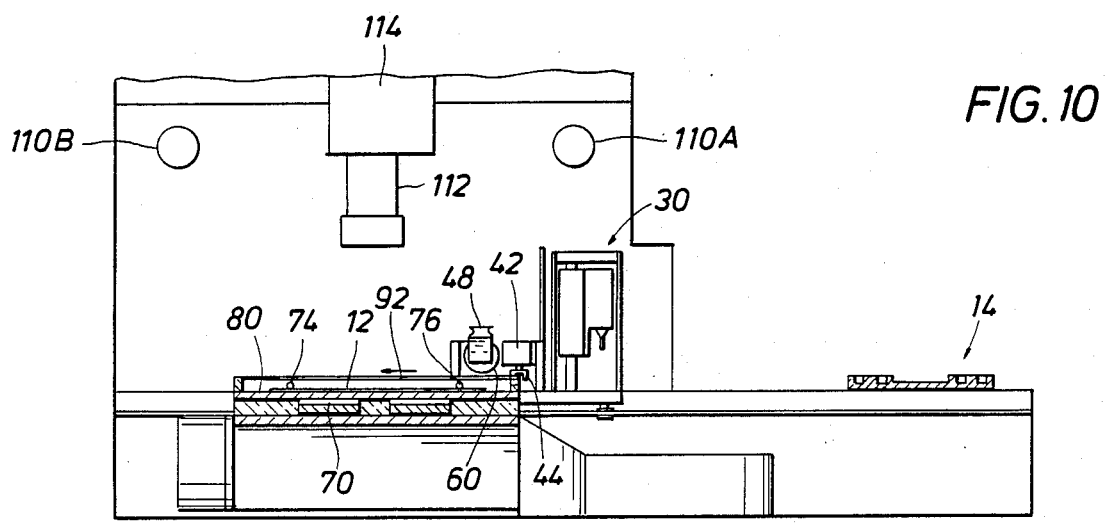

FIG. 10 illustrates the closing of the cover 92 after the slotted arm 44 has been actuated by solenoids 42 to engage holes 93 in the cover 92. FIG. 10 illustrates that the robotic assembly 30 has been moved longitudinally toward the electrophoresis chamber thereby closing the cover 92.

It is assumed that after the cover has been closed, the electrophoresis process of the samples is performed. Such process has been described above but in summary, it is includes applying an electrophoresis voltage to the support medium by means of the posts, electrodes and combination electrode/spreader bars as indicated previously. Simultaneously with application of the electrophoresis current to the support medium 12, current is applied in one direction to the Peltier heating/cooling devices 70. Cooling of the support medium 12 allows a higher electrophoresis current to be applied and thereby allows the entire electrophoresing process to be accomplished with higher speed.

Figure 11:
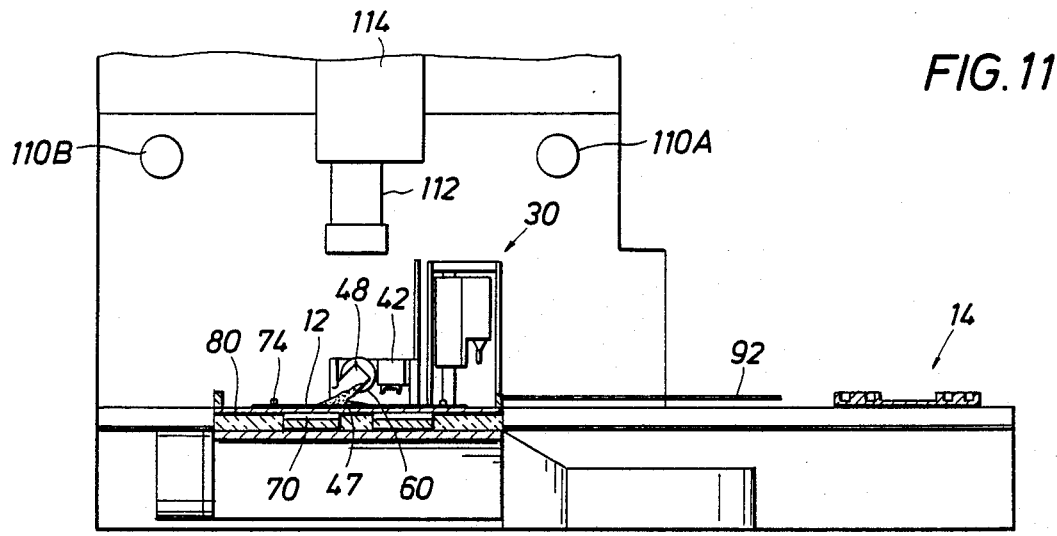

FIG. 11 illustrates the application of reagent 47 from reagent bottles 48. The reagent of such bottles are dumped onto the surface of the support medium 12 by turning the bottle support member 50 by means of motor 60. FIG. 11 indicates that the cover 92 has been previously brought to the open position by the reverse process of that indicated in FIG. 10.

Figure 12:
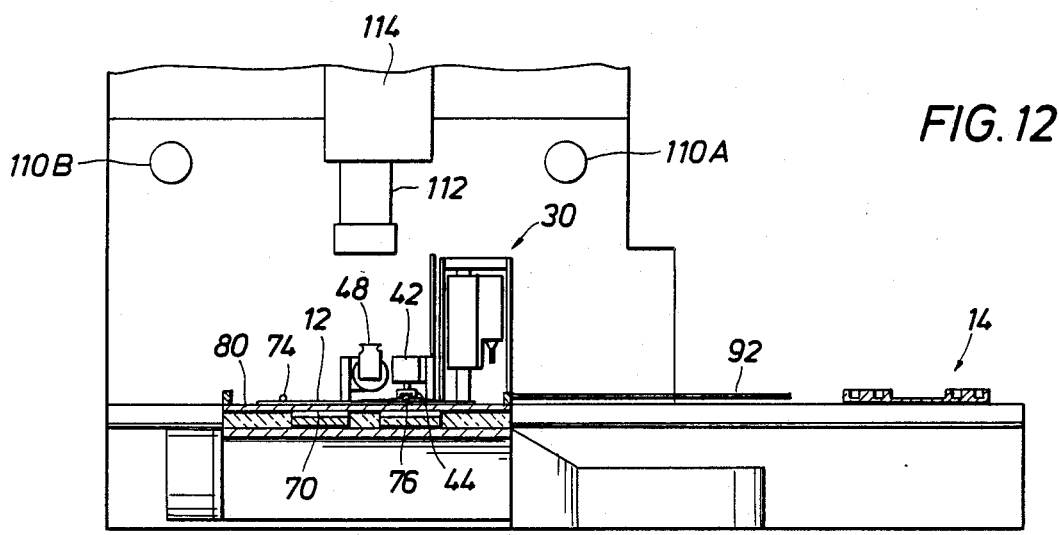

FIG. 12 illustrates the spreading of the reagent across the surface of the support medium 12. Preferably the spreading is accomplished by actuation of the slotted plunger arm 44 so that the slots of both spreader arms are about a bar such as 76. The robotic assembly is then reciprocated longitudinally such that the reagent is spread across the surface of the support medium 12. The other spreader bar 74 may similarly be used in addition to the bar 76 illustrated in FIG. 12 to further spread the reagent on the surface of the support medium 12.

Next, the cover 92 is moved to its closed position in an operation similar to that shown in FIG. 11 and incubation and drying steps are performed. The incubation step calls for the Peltier devices to be operated so as to heat the application plate 80 for a predetermined length of time. The drying step calls for additional drying air to be brought through ducts and across the support medium as illustrated more clearly in FIG. 4.

Figure 13:
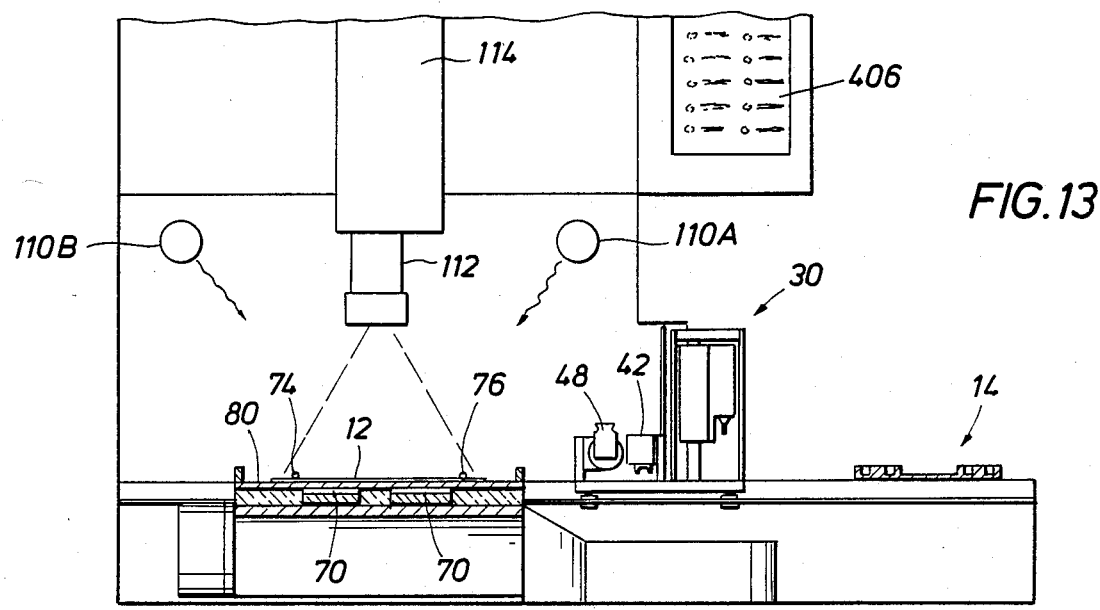

After the incubation and drying steps have been performed, the electronic scanning of the in situ support medium 12 is conducted. As FIG. 13 illustrates, the camera 114/lens 112 system produces an analog signal representative of the field of view of the support medium 12 as illuminated by flourescent lights 110A–110D. An image of such optical signal may be reproduced on CRT 406 mounted directly on the machine. FIG. 13 also illustrates that the robotic assembly 30 is within the opening 101 of the entry side all of the scanning box 100 to substantially reduce outside light from entering the scanning box during optical scanning by the T.V. camera 114.

Description of computer control of machine operations

Figure 14A:
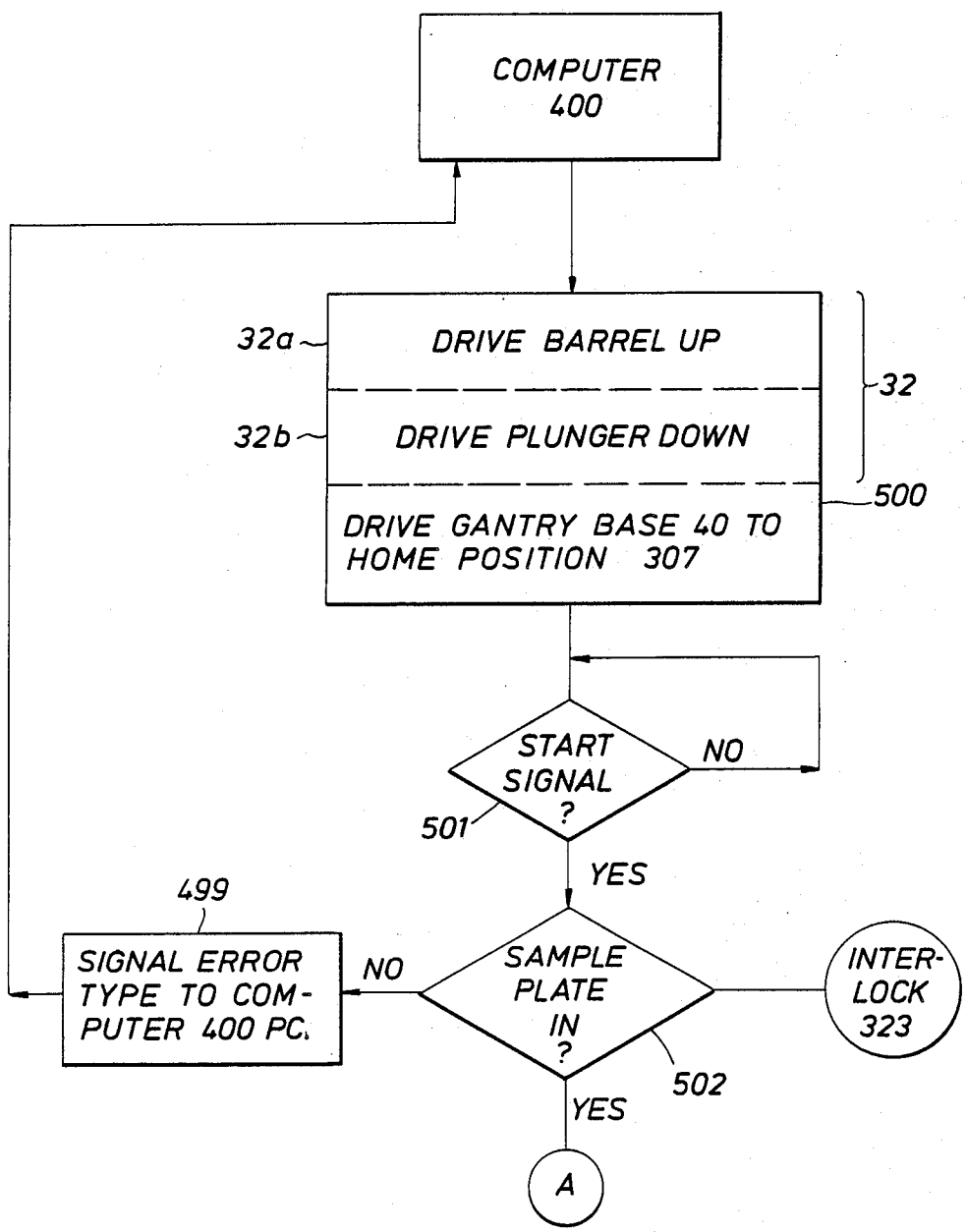

FIGS. 14A–14F illustrate in flow diagram form the control of the machine. FIG. 14A shows that a signal from computer 400 is passed to digital control circuitry for automatic control of the electrophoresis process. As indicated by logic box 500, the pipette assembly is driven to rest position by driving the barrels up as shown in logic box 32a and the plungers down, as shown in logic box 32b. Such control is described in the above-mentioned corresponding U.S. patent application No. 853,201. The gantry base 40 is driven to home position by applying a control signal to motor driver and braking circuit 307 and sensing its position with position detector 316. Next, the computer waits for a start command via serial input/output interface 328, as indicated by logic block 501. The computer then determines by means of logic block 502 if the sample plate 14 has been placed on the base plate 15 of the machine. If a signal is present from interlock circuit 323, control of the process continues along the "YES" path; if the signal from circuit 323 is not present, an error signal is returned to computer 400 as indicated by logic box 499 for printing or displaying an error message to the operator of the machine.

Figure 14B:
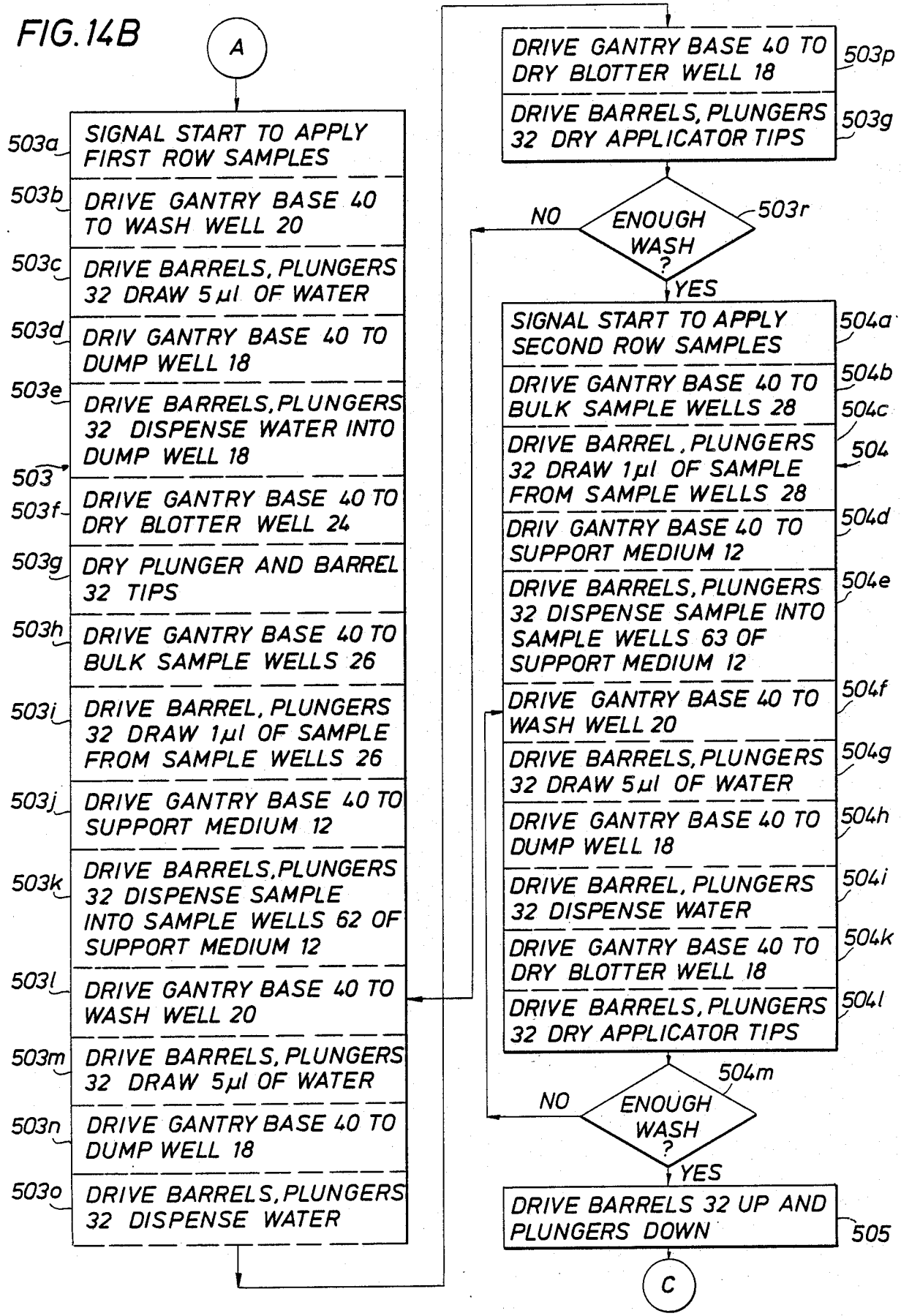

As shown in FIG. 14B, logic blocks 503 apply liquid samples from sample wells 62 to support medium 12. As indicated, functions of washing and drying the pipette tips precede the application of the samples to the support medium and follow such application. For example, a signal is received from logic decision box 502 in logic box 503a to start the procedure for application of first row samples. Next, logic box 503b indicates that the gantry base 40 is driven to wash well 20. Next, as indicated in logic box 503c, the barrels and plungers 32 are driven to draw 5µl of water. Then, as indicated in logic box 503d, the gantry base 40 is driven to dump well 18. Next, as indicated in logic box 503e, the barrels and plungers 32 are driven to dispense water into dump well 18. Then, as indicated in logic box 503f, the gantry base is driven to dry blotter well 24. Next, as indicated by logic box 503g, the plunger and barrel tips 32 are dried on blotter paper of well 24. Next, as indicated by logic box 503h, the gantry base 40 is driven to bulk sample wells 26. As indicated in logic box 503i, the barrels and plungers 32 are actuated to draw one μ1, for example, of sample from sample wells 26. Next, as indicated in logic box 503j, the gantry base 40 is driven to support medium 12. Then, as indicated in logic box 503k, the barrels and plungers 32 are driven to dispense sample into sample wells 62 of support medium 12. Next, as indicated in logic box 503l, the gantry base 40 is driven to wash well 20. As indicated in logic box 503m, the barrels and plungers 32 are driven to draw five μ1 of water, for example. Next, as indicated in logic box 503n, the gantry base 40 is driven to dump well 18. As indicated in logic box 503o, the barrels and plungers are driven to dispense water into the dump well. Next, as indicated in logic box 503p, the gantry base 40 is driven to dry blotter well 18. Then, as indicated in logic box 503g, the barrels and plungers 32 are driven to dry the applicator tips on blotter paper of blotter well 18. Next as indicated by logic box 503r a test is made to determine if there has been a sufficient number of cycles of washing. If no, control is passed to logic block 503l so that another cycle of washing and blotting can be performed. If yes, control is passed to perform similar functions for the second row of samples in logic box 504a. Liquid samples from sample wells 28 are then applied to sample wells 63 of support medium 12. Such function begins by passing logic control from logic box 504a to logic box 504b which drives gantry base 40 to bulk sample wells 28. Next, as indicated by logic box 504c, the barrel and plungers 32 are driven to draw one μ1 of sample from sample wells 28. Next, the gantry base 40 is driven to support medium 12, as indicated by logic box 504d. As indicated by logic box 504e, the barrels and plungers 32 are then driven to dispense sample into sample wells 63 of support medium 12. Next, as indicated by logic box 504f, the gantry base 40 is driven to wash well 20. The pipette tips are again washed. Such washing of the pipette tips is performed as indicated by logic blocks 504g, 504h, 504i, 504k, and 504l in the same way as respective logic blocks 503l, 503m, 503n, 503o, 503p and 503q discussed above. Next, as indicated by logic box 504m, a test is made to determine if there has been a sufficient number of cycles of washing and blotting. If no, control is passed to logic block 504f so that another cycle of washing and blotting can blotting and application steps are similar to those described in U.S. patent application No. 853,201. Next, in logic step 505 the barrels of the pipette assembly 32 are driven up and its plungers are driven down.

Figure 14C:
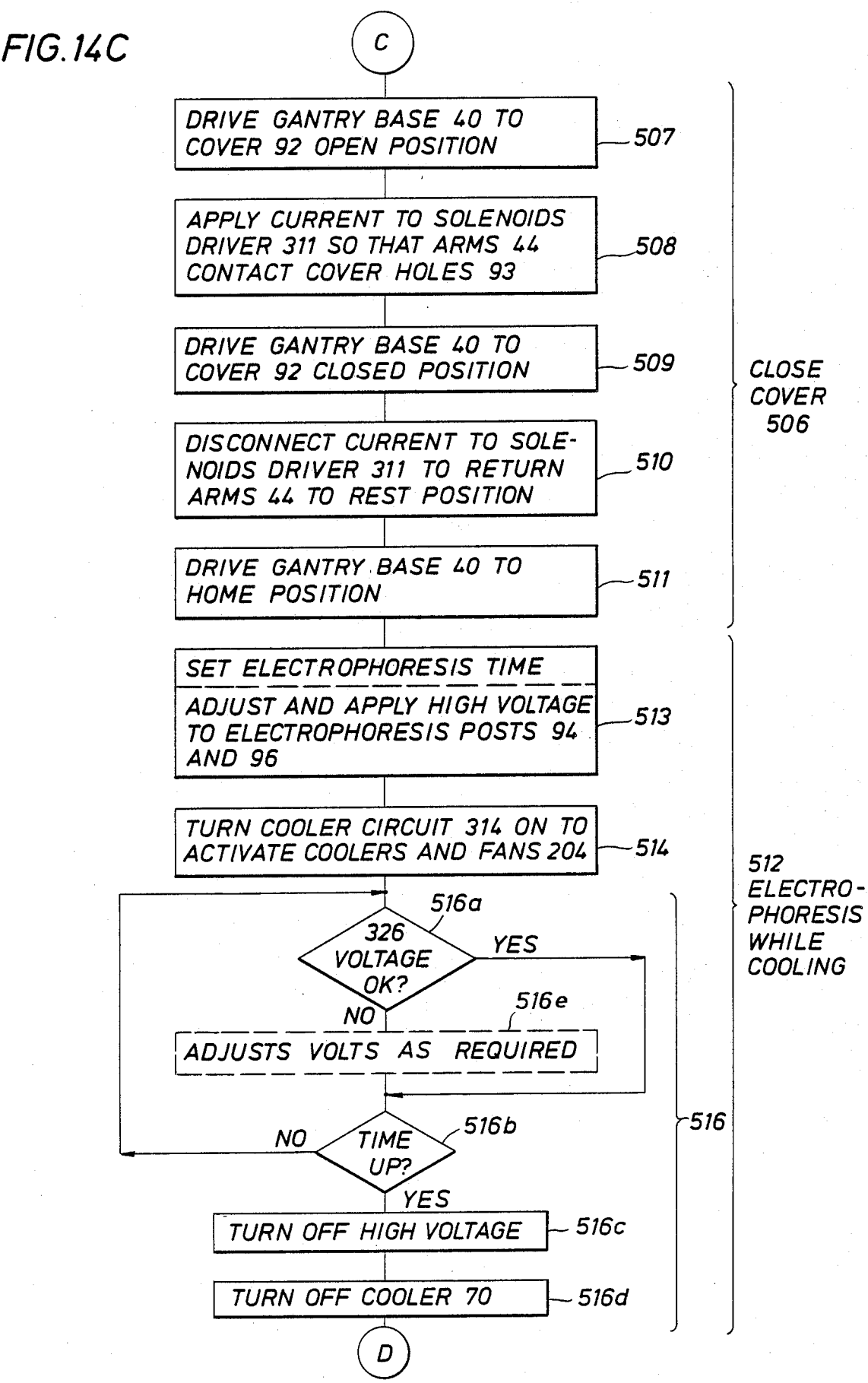

As illustrated in FIG. 14C, a series of steps 506 are performed under digital control circuitry 300 control to close cover 92 over the electrophoresis chamber 13. These steps begin with logic block 507 where the gantry base 40 is driven to the open position of cover 92. Then in step 508, the current is applied to the solenoid drive circuit 311 so that arms 44 are driven downwardly to engage holes 93 in cover 92. Next in logic block 509, the gantry base 40 is driven toward the electrophoresis chamber 13 to the closed position of the cover 92. In logic block 510, current is disconnected from solenoid driven circuit 311 whereby the arms 44 return to their rest position. In block 511, the gantry base 40 is driven to its home position.

Logic blocks 512 are performed to apply electrophoresis current to the support medium 12, while simultaneously cooling it. Logic block 513 sets the time length for the application of electrophoresis current and adjusts and applies high voltage between electrophoresis post pairs 94 and 96. In logic block 514, cooler circuit 314 is activated to turn coolers 70 and fans 204 on. Logic blocks 516 monitor the voltage from circuit 325, monitor the electrophoresis time and then turn off the voltage and coolers. For example, logic box 516a determines if the electrophoresis voltage is proper; if the answer is YES, control is passed to the TIME UP? logic box 516b. If the voltage is not proper, the voltage is adjusted, as indicated in logic box 504e and then control is passed to the TIME UP? logic box 516b. The timer of logic box 516b determines if the electrophoresing time has been proper. If not, control is passed to logic box 516a. If the time for electrophoresing has been of sufficient length, control is passed to logic box 516c where the high voltage for electrophoresing is turned off and then to logic box 516d for turning cooler 70 off.

Turning next to FIG. 14D, logic blocks labeled collectively as 517 describe the steps necessary to open cover 92. Such steps are similar to those of steps 506 to close cover 92 and consequently are not described in detail. In other words, logic blocks 517a, 517b, 517c, 517d and 517e are directly analogous to logic blocks 507, 508, 509, 510 and 511 described above with respect to closing the cover. The blocks labeled collectively as 518 provide the control for applying staining reagent to the surface of the support medium 12. In logic block 519, the gantry base 40 is driven to the support medium 12 to a position approximately mid-way between electrode/spreader bars 74, 76. In logic block 520, the reagent motor drive is actuated thereby rotating the reagent bottles 48 operably applying reagent to the top surface of the support medium 12. The reagent motor drive is then driven in the opposite direction to return the reagent bottle support member 50 to its rest position.

The logic blocks collectively identified by the reference number 521 describe the steps necessary for spreading the staining reagent across the top surface of support medium 12. In logic block 522, the gantry base 40 is moved until solenoids 42 are directly above electrode/spreader bar 74. In block 523, current is applied to solenoid driver circuit 311 so that arms 44 are extended downwardly such that the slots 44a of the arm 44 "grip" or partially envelope the spreader bar 74. In logic step 524, the gantry base 40 is driven toward the second wells 63 and then are driven again to the position of electrode posts 94. The current to the solenoid driver circuit 311 is disconnected in logic block 525 to return the arms 44 to the rest position. The logic blocks labeled 526, 527, 528, 529, control the spreading of the reagent by spreading electrode/spreader bar 76 across the surface of the support medium and returning the solenoid arms 44 to their rest position.

The cover 92 is then closed according to the logic blocks 530, identical to those labeled 506 performed earlier in automatic process. In other words, logic blocks 530a, 530b, 530c, 530d and 530e are the same as logic blocks 507, 508, 509, 510 and 511 as described above.

Figure 14E:
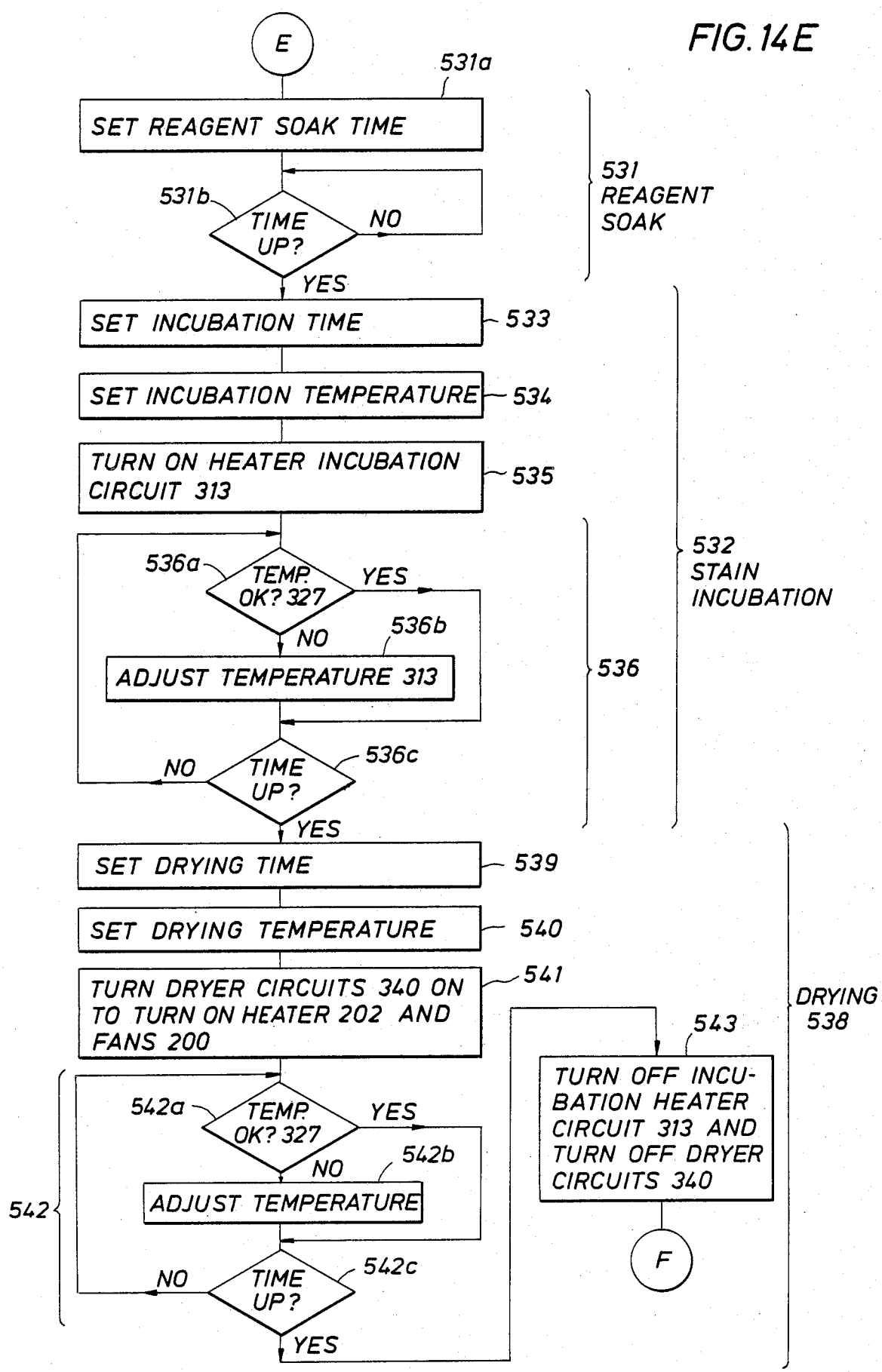

Turning next to FIG. 14E, the process continues with logic steps labelled collectively as 531 for reagent soak. The digital control circuitry 300 in these steps allows a sufficient time to pass between application of the reagent to the surface of the support medium and the start of the incubation period. For example, the logic box 531a sets the reagent soak time and logic box 531b determines if such time has elapsed. If NO, control is again paired to logic box 531b. If YES, control is passed to logic block 533.

The logic steps labelled collectively as stain incubation 532 begin with step 533 for setting the incubation time and step 534 for setting the incubation temperature. The incubation heater circuit 313 is turned on in logic step 535. Logic steps 536 monitor incubation temperature from sensor 327 and passes control to drying steps 538. For example, the logic box 536a determines if the incubation temperature is proper. If it is, control is passed to logic box 536c which determines if the incubation time has elapsed. If the incubation temperature is not proper, control is passed to logic box 536b for adjusting the level of heater incubation circuit 313. Thereafter, control is passed to time monitor logic box 536c. If the logic box 536c determines that the incubation time is not up, control is passed again to logic box 536a for another determination of proper temperature from sensor 327. If the logic box 536c determines that incubation time has been passed, control is directed to logic box 539 to begin the drying steps 538.

The logic steps labelled collectively as drying 538 begin with steps 539 and 540 where drying time and drying temperature are set. In logic step 541 dryer circuits 340 are activated for turning on heater 202 and fans 200. Steps 542 monitor drying temperature from temperature monitor 327 and monitors the drying time. For example, logic box 542a determines if the drying temperature is proper. If it is, control is passed to logic box 542c which determines if the drying time has elapsed. If the drying temperature is not proper, control is passed to logic box 542b for adjusting the level of the driver circuits 340. Thereafter, control is passed to time monitor logic box 542c. If time monitor logic box 542c determines that drying time has not elapsed, control is passed again to logic box 542a for another determination of proper drying time is up, control is passed to logic box 543. Step 543 turns off the incubation heater circuit 313 and the dryer circuit 340.

FIG. 14F shows that cover 92 is again opened under control of logic steps labelled collectively as 544. Such steps are identical to those labeled above as steps 517. For example, logic boxes 544a, 544b, 544c, 544d and 544e are exactly the same as logic boxes 517a, 517b, 517c, 517d and 517e. Control is then passed to logic step 545 where a determination is made by computer 400 as to whether or not lamps 100A–100D are on. If not, control is passed to computer 400 which then issues a signal to turn them on in logic block 546. On receipt from a signal of logic block 547 indicative that the lights have been turned on, control is passed to logic block 548 where the video image from camera 104 is captured and stored in memory. The lights 110A–110D are turned off under control of logic block 549.

The computer 400 then performs densitometric processing in logic step 550 according to known methods of determining the relative densities of components of the samples which have bene longitudinally separated as a result of the electrophoresis process. Graphical outputs are displayed on cathode ray tubes 405 and 406 and printed reports are output on printer 408 as indicated by logic blocks 551 and 552.

Various modifications to the automatic electrophoresis machine and methods described above may be apparent to those skilled in the art which do not depart from the spirit of the invention. The description above is employed for setting forth the preferred embodiment of the invention and should be interpreted as illustrative, but not limitative.

What is claimed is:

1. In a system including a scanning box substantially enclosing a plate for placement of a support medium, said support medium having a plurality of laterally spaced sample tracks extending longitudinally across said medium, said system having fluorescent light means secured within said box for fluorescently lighting said support medium and having an imaging device directed toward said support medium for generating video signals representative of the light intensity of said support medium, said system further including computer means responsive to said video signals for storing a pixel matrix of intensity levels of said video signal, a method for producing a correction matrix for correcting said imaging device for non-linear imaging effects comprising the steps of, placing a test support medium on said plate,
illuminating said test support medium with said fluorescent light means,
generating video signals representative of the light intensity of the surface of said test support medium,
storing in said computer means a pixel matrix of intensity levels of said video signals of said test support medium,
separating said pixel matric into a plurality of longitudinal tracks each comprising a plurality of pixel rows corresponding to said sample tracks,
averaging the lateral intensity pixels for each track for each longitudinal position of the matrix and storing an average intensity matrix including an average intensity pixel value for each track at each longitudinal position of the matrix,
identifying from said average intensity matrix the track pixel having the greatest average intensity value, and
dividing each track average pixel intensity value into said greatest average intensity value and replacing each intensity value of said average intensity matrix with the result of each such division to create said correction matrix for correcting said imaging device for non-linear imaging effects.

2. A method of determining relative components of a liquid sample in an apparatus having an application plate longitudinally disposed on a base and an electrophoresed support medium removably secured to a top surface of said application plate, said support medium having a plurality of laterally spaced sample tracks extending longitudinally across said medium, said apparatus having a scanning box substantially enclosing said support medium and having fluorescent light means secured to said box for fluorescently lighting said electrophoresed support medium and having an imaging device directed toward said support medium for generating video signals representative of the light intensity of said electrophoresed medium, said apparatus further including computer means responsive to said video signals for storing a pixel matrix of intensity levels of said video signals, said computer means having stored therein a correction matrix including pixel correction factors corresponding to said sample tracks of said electrophoresed support medium as a function of the longitudinal position of the matrix, the method comprising the steps of, illuminating said electrophoresed support medium with said fluorescent light means, generating video signals representative of the light intensity of the surface of said electrophoresed support medium, storing in said computer mean a pixel matrix of intensity levels of said video signals of said electrophoresed support medium, separating said pixel matrix into a plurality of longitudinal tracks each comprising a plurality of pixel rows corresponding to said sample tracks, averaging the lateral intensity pixels for each track for each longitudinal position of the matrix and storing an average intensity matrix including an average intensity pixel value for each track at each longitudinal position of the matrix, multiplying each element of the average intensity matrix by a corresponding element of said correction matrix and replacing each element with the product of such multiplication to generate a corrected intensity matrix of said electrophoresed support medium, and performing a densitometric analysis of said corrected intensity matrix to determine the relative components which have been electrophoresed in each of said plurality of laterally spaced sample tracks which extend longitudinally across said medium.

* * * * *